(12) United States Patent
Berkland et al.

(10) Patent No.: US 9,675,636 B2
(45) Date of Patent: Jun. 13, 2017

(54) MICELLE SEQUESTERING POLYMERS

(71) Applicant: UNIVERSITY OF KANSAS, Lawrence, KS (US)

(72) Inventors: Cory Berkland, Lawrence, KS (US); Jian Qian, Lawrence, KS (US); Bradley Paul Sullivan, Shawnee, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 0 days.

(21) Appl. No.: 14/608,664

(22) Filed: Jan. 29, 2015

(65) Prior Publication Data
US 2015/0216896 A1    Aug. 6, 2015

Related U.S. Application Data

(60) Provisional application No. 61/934,299, filed on Jan. 31, 2014.

(51) Int. Cl.
*A61K 31/785*    (2006.01)
*C08F 220/34*    (2006.01)

(52) U.S. Cl.
CPC .......... *A61K 31/785* (2013.01); *C08F 220/34* (2013.01)

(58) Field of Classification Search
None
See application file for complete search history.

(56) References Cited

U.S. PATENT DOCUMENTS

| 5,367,009 A * | 11/1994 | Inoue | B01F 17/005 106/236 |
| 7,776,319 B2 * | 8/2010 | Alpern | A61K 9/1635 424/490 |
| 2006/0069203 A1 * | 3/2006 | Lewis | A61K 9/1075 524/556 |

OTHER PUBLICATIONS

Datta et al., British Medical Journal, 1963, pp. 216-219.*
Kuron et al., Atherosclerosis, 1980, 37, 353-360.*
Zhang et al., European Polymer Journal, 2006, 42, 2959-2967.*
Dai et al., Langmuir, 2003, 19, 5175-5177.*
BASF, Technical Information, 2015, pp. 1-3.*

* cited by examiner

*Primary Examiner* — Abigail Fisher
(74) *Attorney, Agent, or Firm* — Reed Smith LLP; Robert R. Riddle; Matthew S. Gibson

(57) ABSTRACT

A polymer composition for sequestering lipid-bile acid micelles in the gastrointestinal (GI) tract is provided. The polymer composition comprises a copolymer of a pH-sensitive monomer and one or more of positively-charged monomers. The polymer composition is able to bind micelles under various physiological conditions in the GI tract and possesses the ability to flocculate the bound micelle upon exposure to a particular pH. The flocculation of the polymer:micelle complex prevents absorption of the micelle thereby causing the polymer:micelle complex to be eliminated with the fecal matter. Thus, the polymer composition described herein may be effective in reducing cholesterol, bile acid, and/or triglyceride levels and promote weight loss.

15 Claims, 22 Drawing Sheets
(8 of 22 Drawing Sheet(s) Filed in Color)

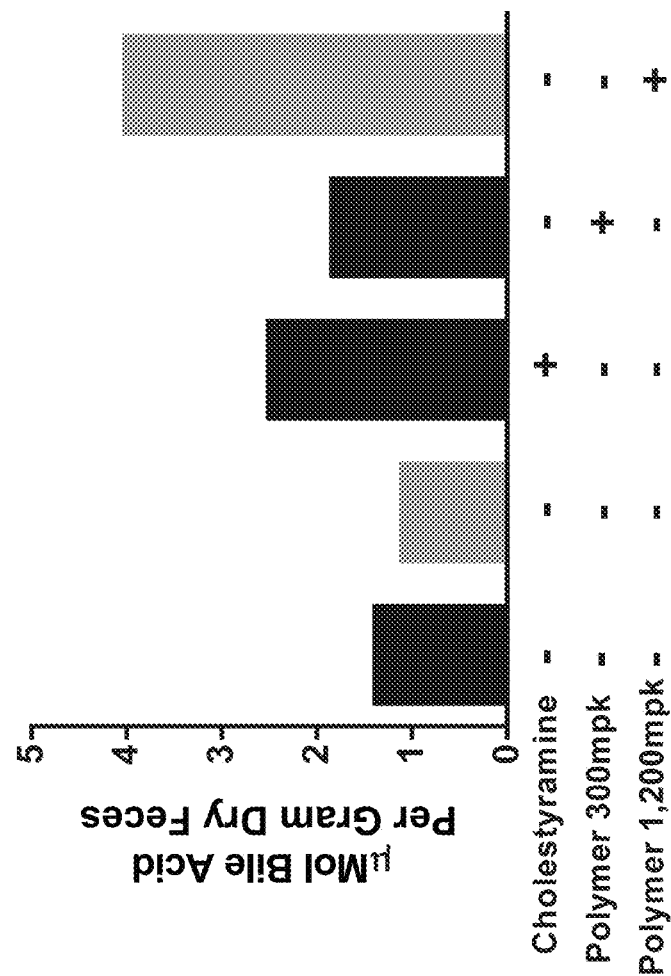

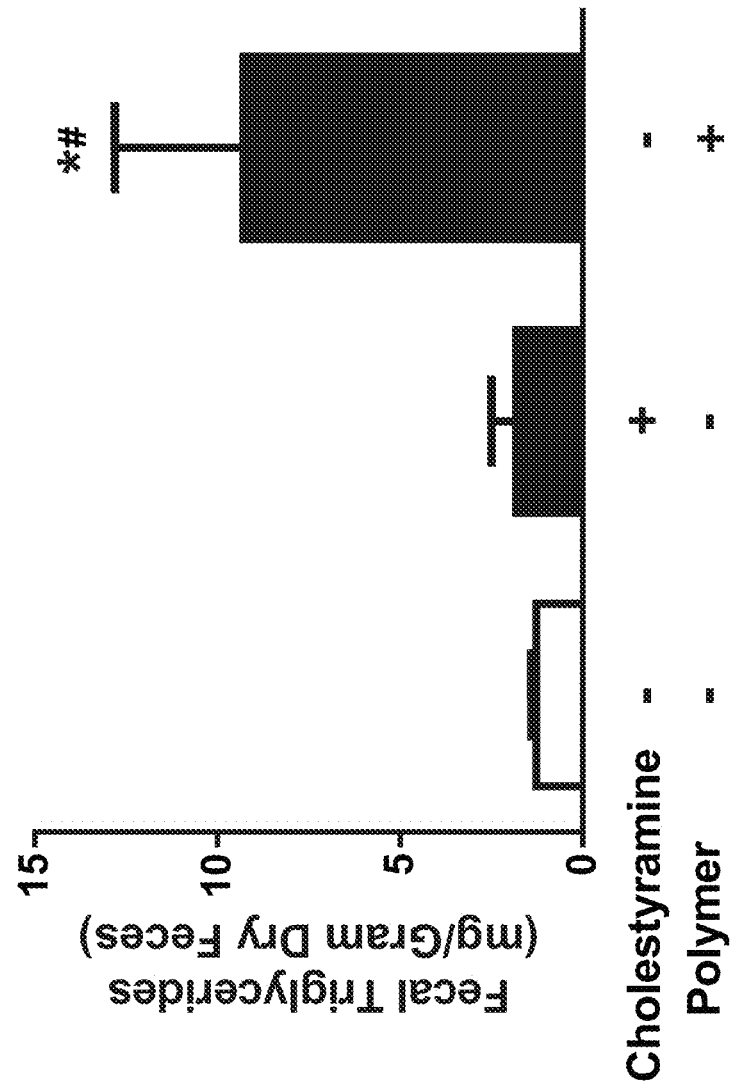

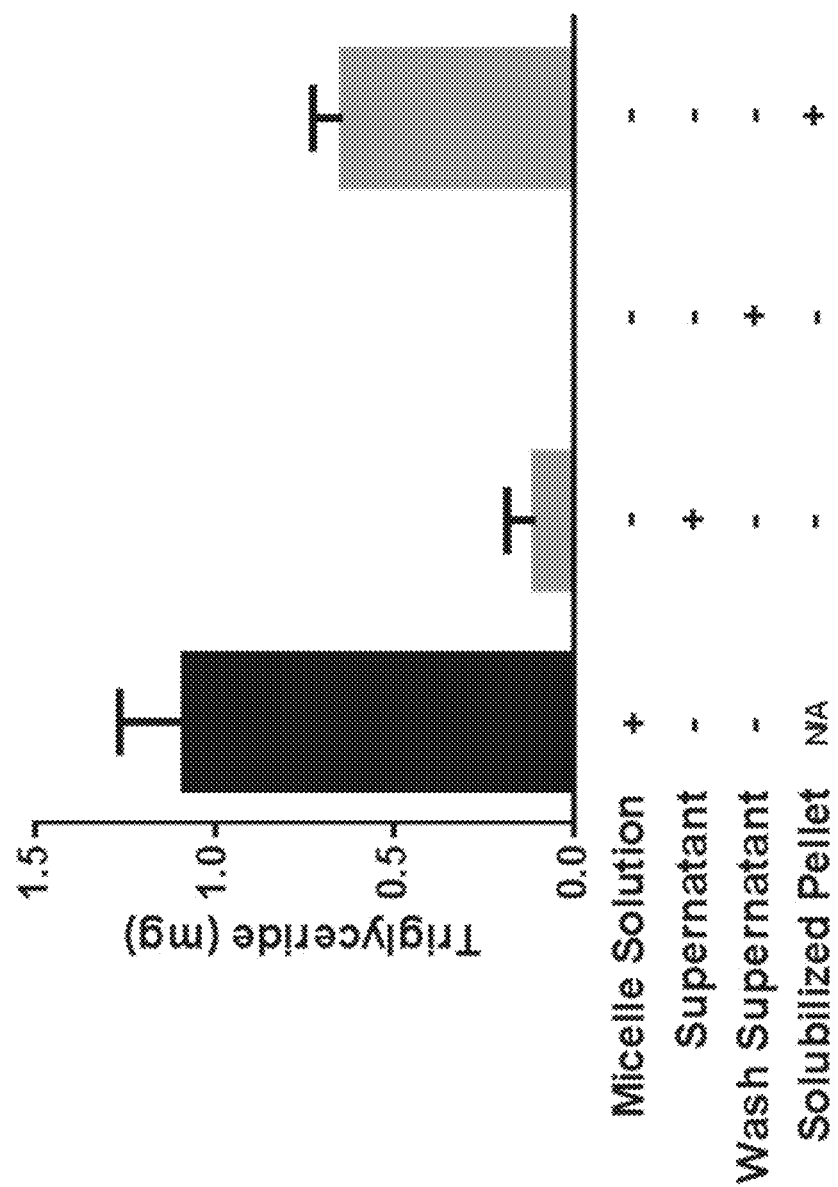

MICELLE SEQUESTERING POLYMERS

CROSS REFERENCE TO RELATED APPLICATIONS

The present application claims priority to U.S. Provisional Application No. 61/934,299 filed on Jan. 31, 2014, which is incorporated herein by reference in its entirety.

BACKGROUND

Over the past quarter century, the rate of patients being classified as overweight or obese has increased at an alarming rate and now affects up to 35% of the population and direct health care costs are estimated to be greater than $150 billion/year. Importantly, being overweight (or obese) is a major risk factor for developing cardiovascular disease, Type II diabetes, and other diseases such as cancer. Many options exist to treat obese patients and their clinical manifestations of metabolic syndrome including several FDA approved therapies; however, to date there is still no uniformly consistent long term efficacious pharmacotherapy with limited tolerable side effects and exceptional long term patient compliance. Development of a pharmacotherapy that has exceptional long term patient compliance, efficacy in reducing excess (adipose) weight, and safety profile would have substantial socioeconomic impact globally.

SUMMARY

The present disclosure is therefore directed, in one embodiment, to a composition comprising a polymer-based fat and bile acid sequestrant (also referred to herein as a "micelle sequestrant polymer") and methods of using such to promote weight loss, reduce cholesterol and lipid absorption, and other clinical manifestations of or conditions associated with obesity and metabolic syndrome. In certain embodiments, a composition comprising a copolymer of a pH-sensitive monomer and of at least one positively-charged monomer is provided. In certain embodiments, the copolymer has a micelle sequestration efficiency of about 50% to about 100% or from about 85% to about 100%.

In certain embodiments, the polymer composition is capable of binding a lipid/bile acid-containing micelle under physiological conditions associated with the small intestine. For example, the polymer composition is capable of binding a micelle at a pH from about 4.0 to about 8.0 and further, from about 5.0 to about 7.0 and in one example, less than about 6.0. Upon binding the micelle, the polymer compositions of the present disclosure are capable of inducing flocculation of the polymer:micelle complex at pHs of about 5.0 to about 8.0 or from about 5.5 to about 7.5, or from about 6.0 to about 7.0.

In certain embodiments, the pH-sensitive monomer of the present polymer compositions can transition from a soluble phase to an insoluble phase upon a particular pH change. For example, the pH-sensitive monomer transitions at a pH from about 4.0 to about 9.5 or from about 5.0 to about 8.5 or from about 6.0 to about 7.0. For example, the pH-sensitive monomer is a tertiary amine. In yet another example, the pH-sensitive monomer is selected from the group consisting of 2-vinylpyridine, 2-(Diethylamino)ethyl methacrylate, 2-(dibutylamino)ethyl methacrylate, and 2-(diisopropylamino)ethyl methacrylate.

In certain embodiments, the positively-charged monomer of the present polymer compositions is a salt that retains its charge across a wide range of physiological pH conditions. For example, the positively-charged monomer is an ammonium cation. In other embodiments, the positively-charged monomer is a tertiary or quaternary amine. For example, the positively-charged monomer is selected from the group consisting of (vinylbenzyl)trimethylammonium chloride, [2-(methacryloyloxy)ethyl]trimethylammonium chloride and diallyldimethylammonium chloride A method of using the present composition to treat a variety of metabolic-related conditions is also provided. In one instance, a polymer composition described herein is administered to an organism to promote weight loss. In another instance, a polymer composition described herein is administered to an organism having a metabolic syndrome. In yet another instance, a polymer composition described herein is administered to an organism having elevated triglycerides, cholestasis, hypercholesterolemia or other related diseases. In yet another instance, a polymer composition described herein is administered to an organism suffering from obesity or also suffering from elevated triglycerides or hypercholesterolemia.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some specific example instances of the disclosure may be understood by referring, in part, to the following description and the accompanying drawings.

[2-(Methacryloyloxy)ethyl]trimethylammonium chloride-co-(Vinylbenzyl)trimethylammonium chloride) (PDBA-PMAM10-PVBA20) (black square), and a high dose (1200 mg/kg) of PDBA-PMAM10-PVBA20 (gray square).

Figure 9A:
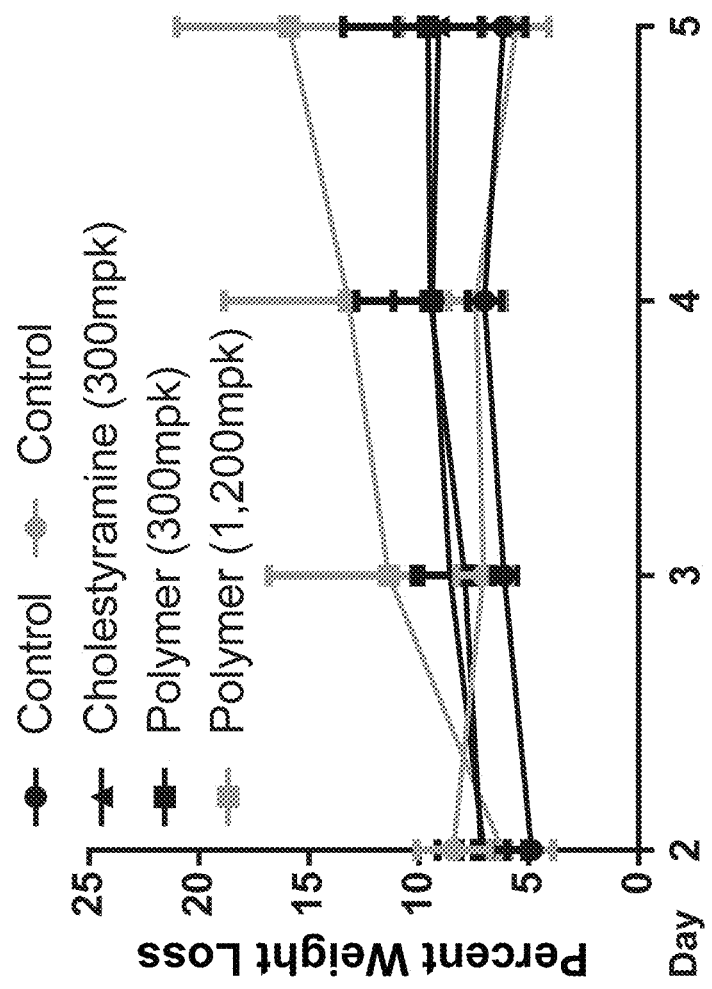
FIG. 9A provides a graph representing percent weight loss of mice fed a standard diet at various days during daily administration of control ($H_2O$) for low dose (black circle), control ($H_2O$) for high dose (gray circle), 300 mg/kg Cholestyramine (black triangle), a low dose (300 mg/kg) of poly(2-(Dibutylamino)ethyl methacrylate hydrochloride-co-
Figure 9B:
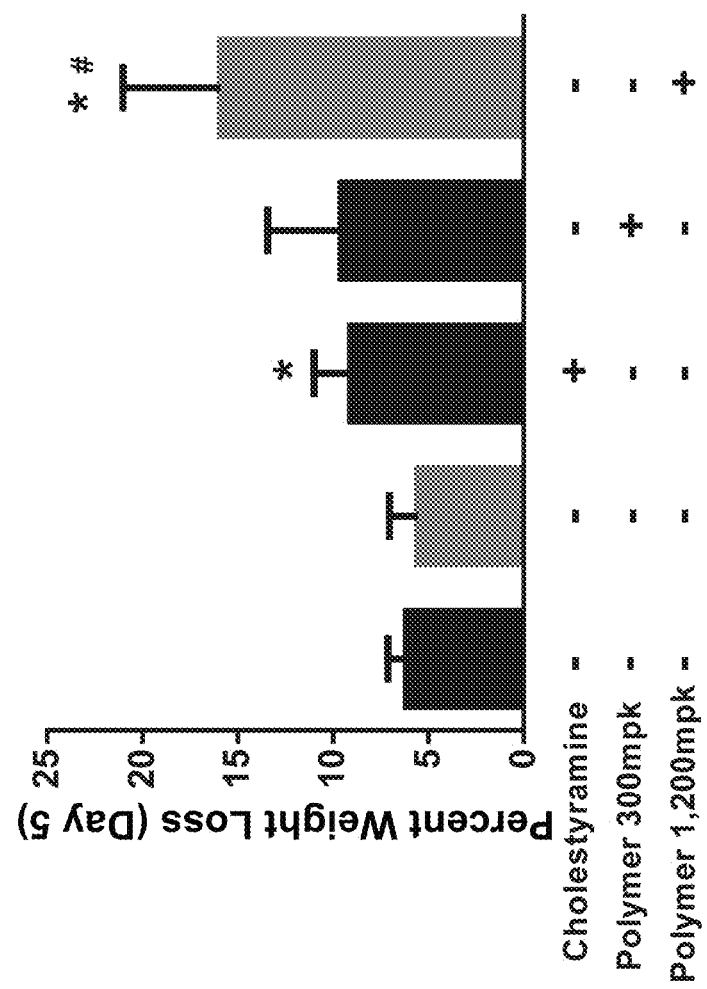

FIG. 9B provides a bar graph representing percent weight loss for day 5 of the experimental groups described in FIG. 9A.

FIG. 9C provides a bar graph representing µMol of bile acid per gram dry feces of the experimental groups described in FIG. 9A.

Figure 9D:
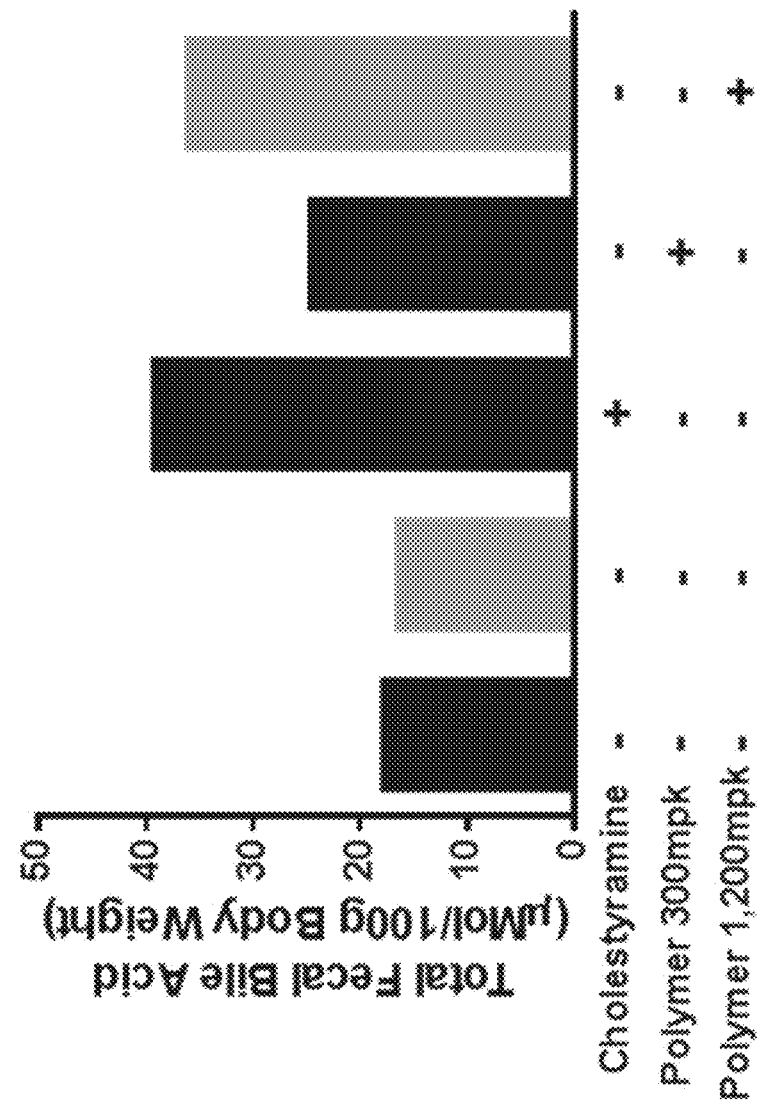

FIG. 9D provides a bar graph representing the total fecal bile acid content per 100 grams body weight for the experimental groups described in FIG. 9A.

Figure 10A:
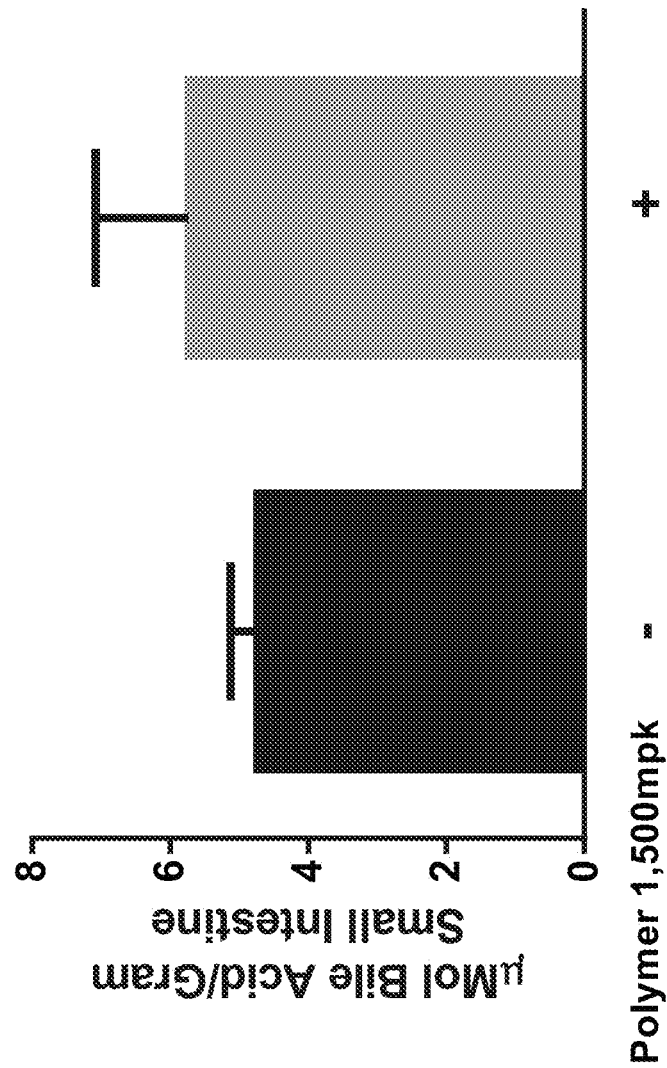

FIG. 10A provides a bar graph representing the amount of bile acid per gram of small intestine in mice receiving vehicle control ($H_2O$) versus mice receiving 1,500 mg/kg polymer composition (PDBA-PMAM10-PVBA20).

Figure 10B:
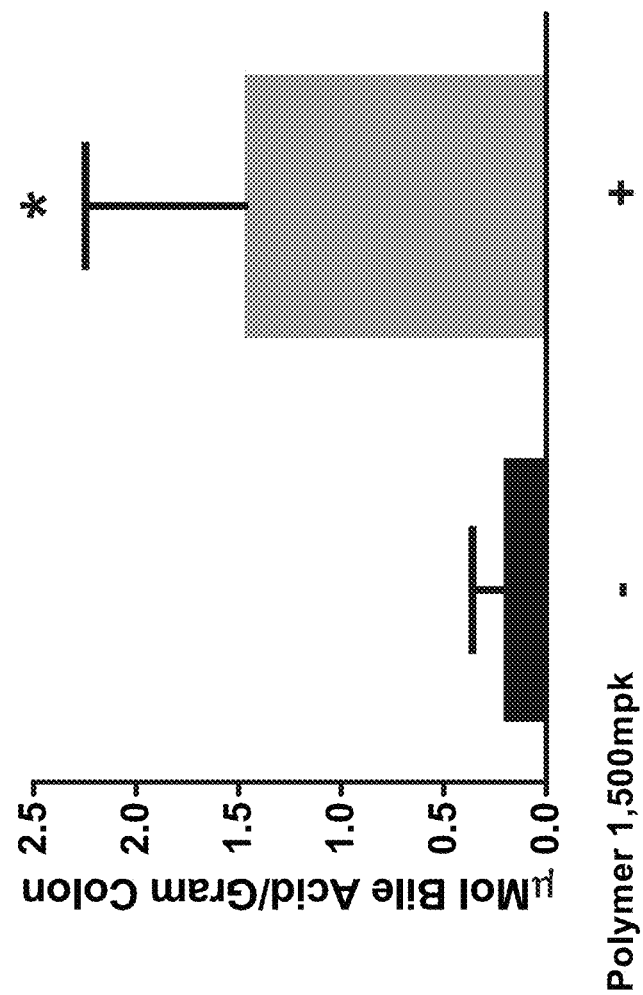

FIG. 10B provides a bar graph representing the amount of bile acid per gram of colon in mice receiving vehicle control ($H_2O$) versus mice receiving 1,500 mg/kg polymer composition (PDBA-PMAM10-PVBA20).

Figure 11A:
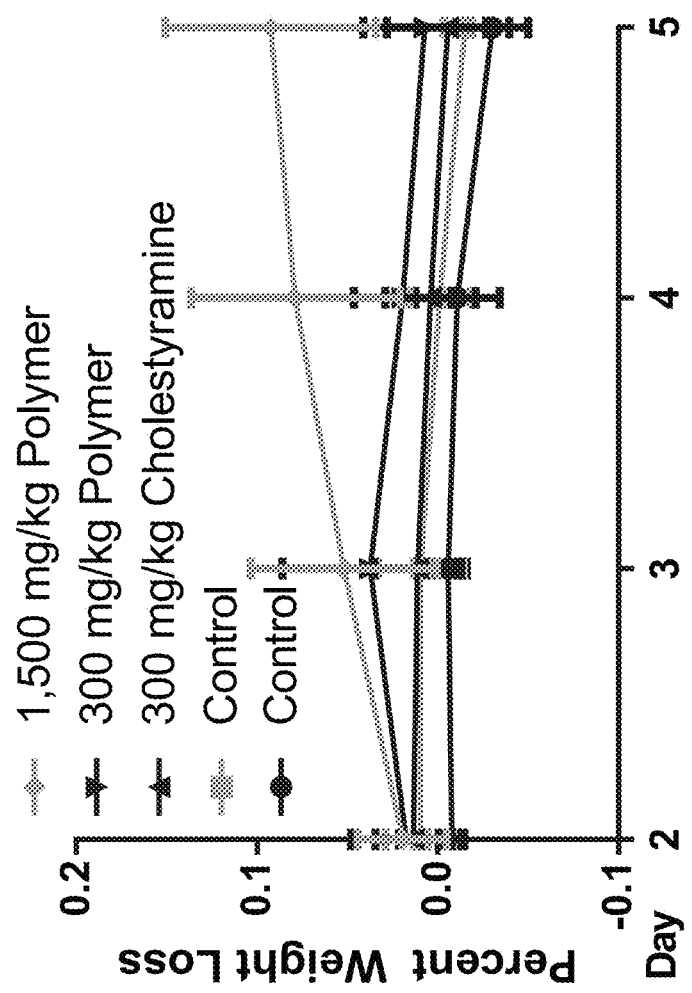

FIG. 11A provides a graph representing percent weight loss of mice fed a high fat diet at various days during daily administration of control ($H_2O$) for low dose (black circle), control ($H_2O$) for high dose (gray square), Cholestyramine (300 mg/kg; black upright triangle), a low dose (300 mg/kg) of polymer composition of the present disclosure (PDBA-PMAM10-PVBA20) (black upside down triangle), and a high dose (1500 mg/kg) of PDBA-PMAM10-PVBA20 (gray circle).

Figure 11B:
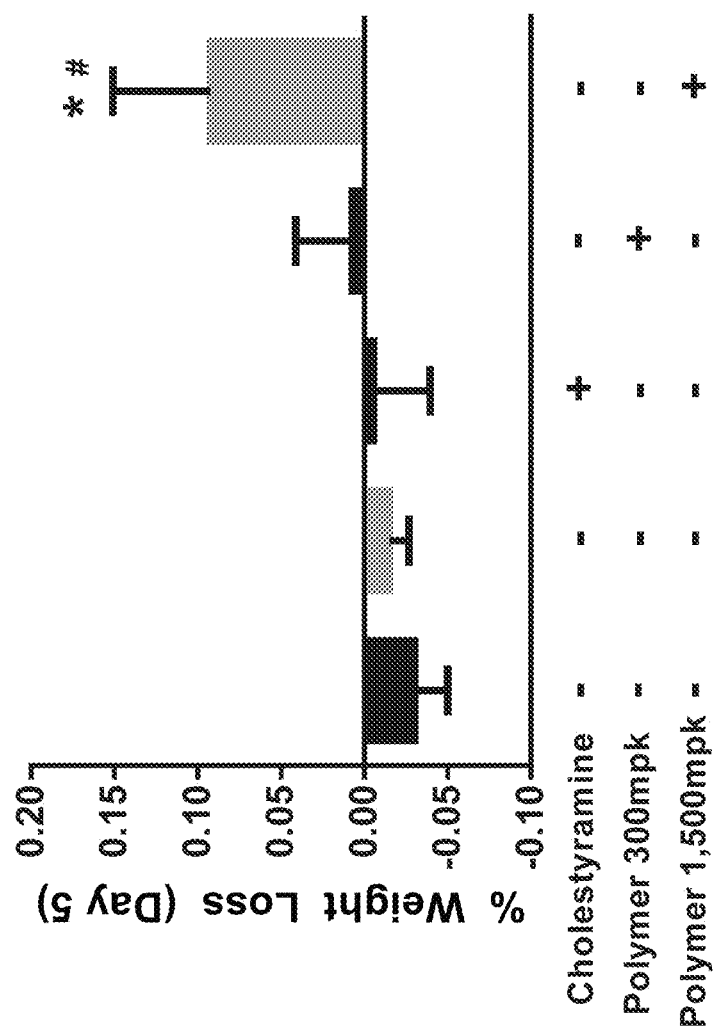

FIG. 11B provides a bar graph representing percent weight loss for day 5 of the experimental groups described in FIG. 11A.

Figure 11C:
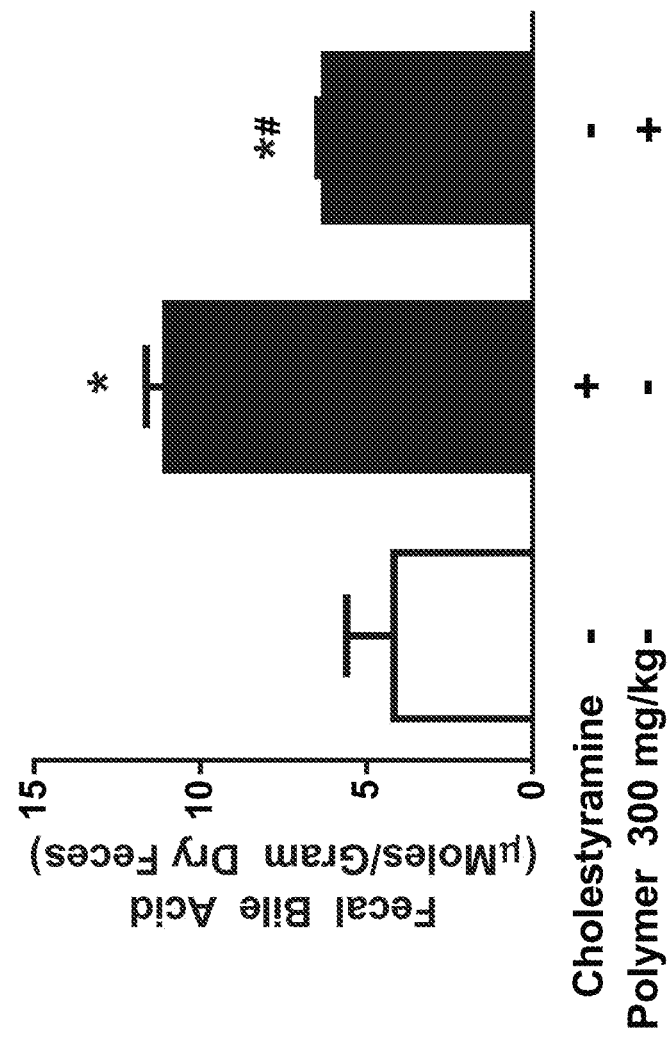

FIG. 11C provides a bar graph representing amount of bile acid (µMole/gram dry feces) in mice receiving either vehicle control ($H_2O$), Cholestyramine (300 mg/kg), or PDBA-PMAM10-PVBA20 (300 mg/kg).

FIG. 11D provides a bar graph representing the amount of triglycerides per gram feces in mice receiving either vehicle control ($H_2O$), Cholestyramine (300 mg/kg), or PDBA-PMAM10-PVBA20 (300 mg/kg).

Figure 12A:
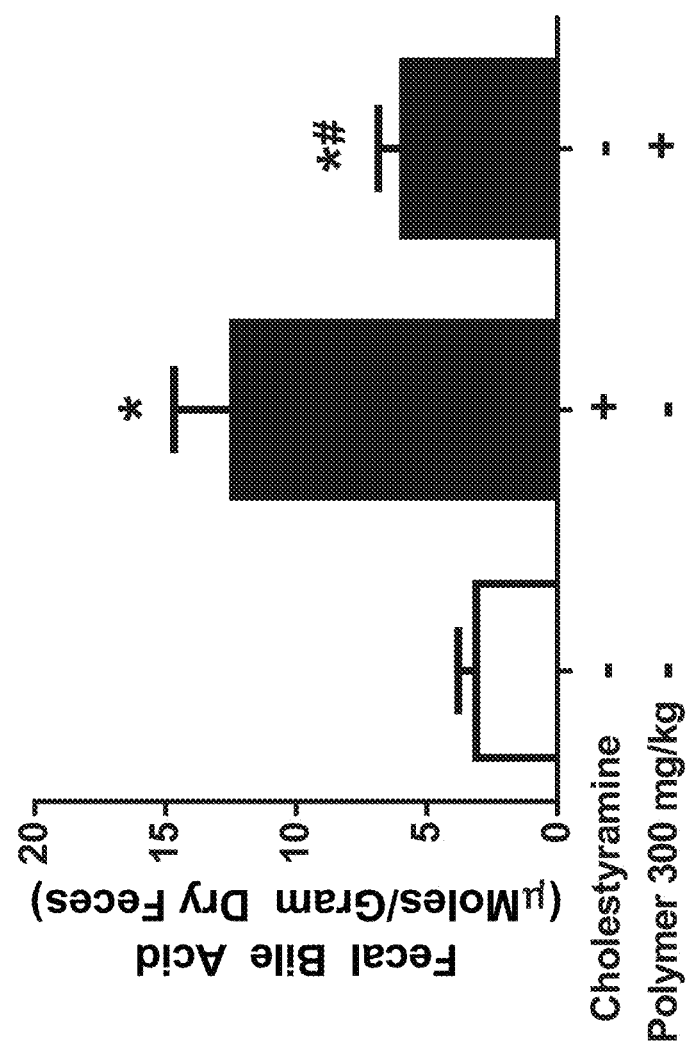

FIG. 12A provides a bar graph representing amount of bile acid (µMole/gram dry feces) in mice receiving either control high fat diet, high fat diet containing 0.5% cholestyramine, or high fat diet containing 0.5% PDBA-PMAM10-PVBA20.

Figure 12B:
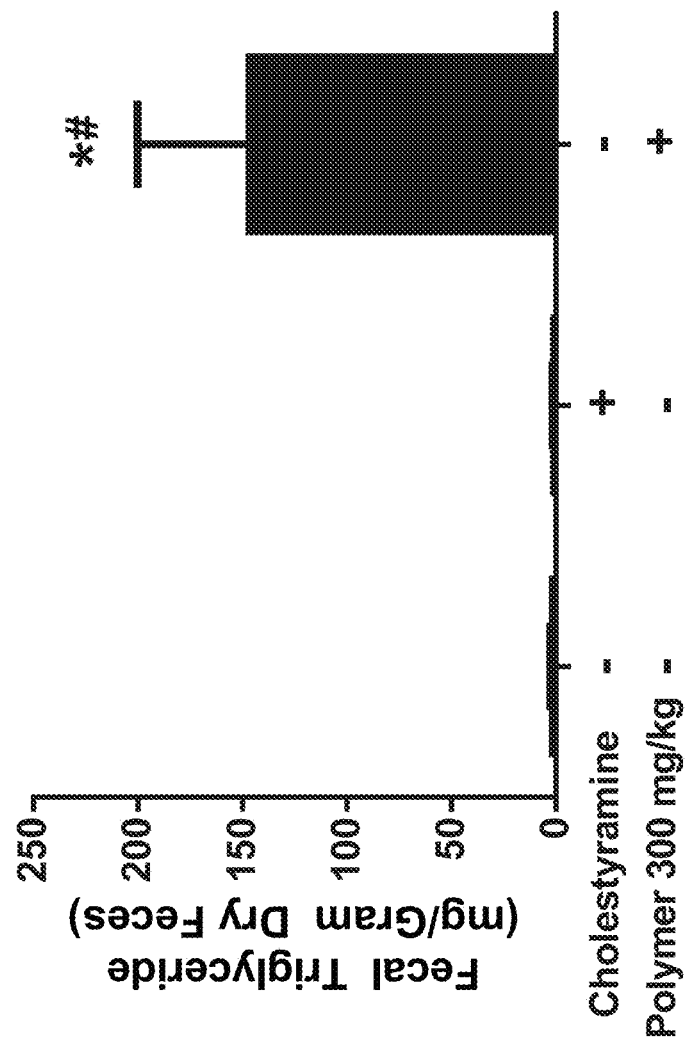

FIG. 12B provides a bar graph representing amount of triglycerides (mg/gram dry feces) in mice receiving either control high fat diet, high fat diet containing 0.5% cholestyramine, or high fat diet containing 0.5% PDBA-PMAM10-PVBA20.

FIG. 13A provides a bar graph representing the total triglyceride content of micelle solution (black bars), triglyceride content left in the micelle solution supernatant after PDBA-PMAM10-PVBA20, was flocculated out of solution via a pH change to approximately pH-8.0 (Supernatant), triglyceride content of the pellet wash buffer (Wash Supernatant), and the triglyceride content of the solubilized PDBA-PMAM10-PVBA20 pellet (Solubilized Pellet).

Figure 13B:
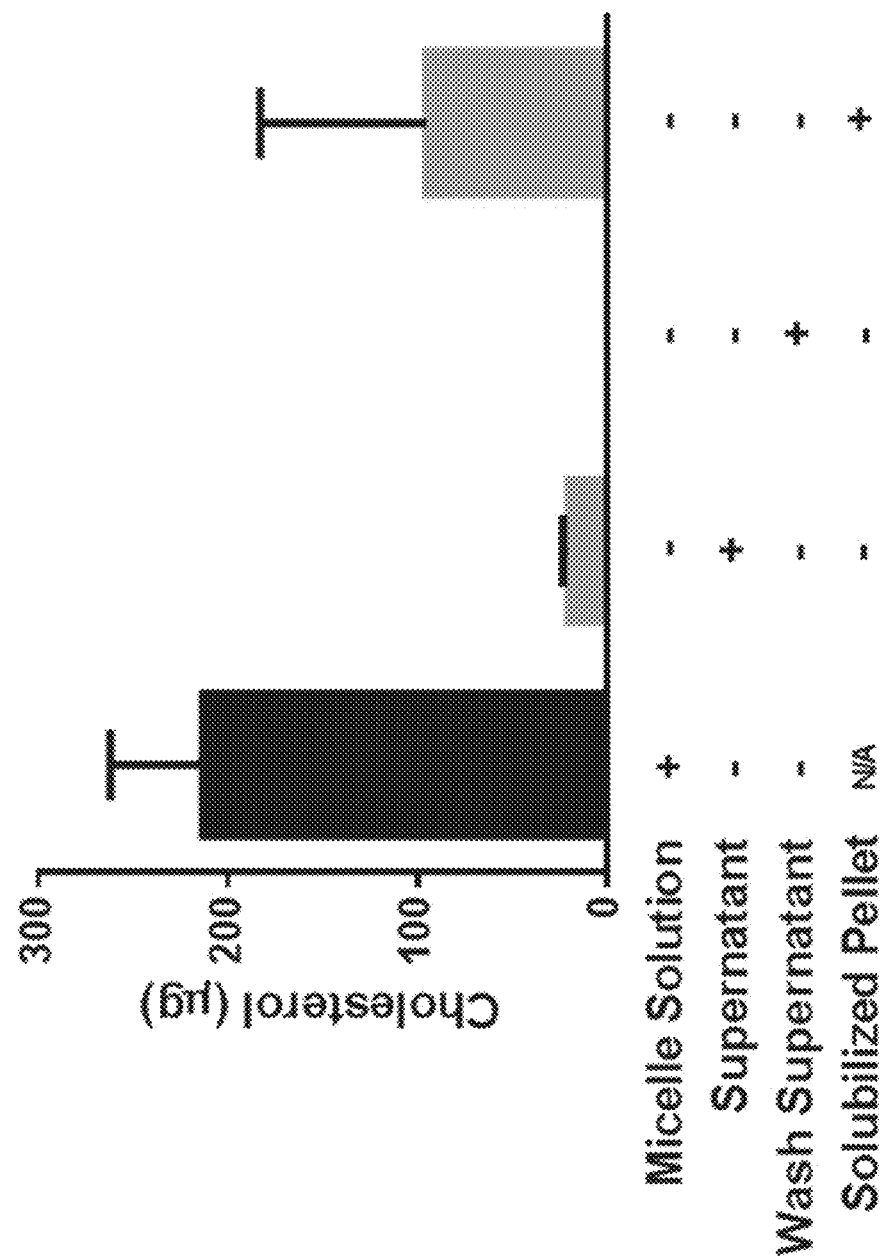

FIG. 13B provides a bar graph representing the cholesterol FIG. 13B provides a bar graph representing the cholesterol content of micelle solution (black bars), cholesterol content left in the micelle solution supernatant after PDBA-PMAM10-PVBA20 was flocculated out of solution via a pH change to approximately pH-8.0 (Supernatant), cholesterol content of the pellet wash buffer (Wash Supernatant), and the cholesterol content of the solubilized PDBA-PMAM10-PVBA20 pellet (Solubilized Pellet).

DESCRIPTION

The present disclosure provides, according to certain embodiments, polymer compositions and methods for using such composition to treat metabolic-related conditions.

In general, the polymer compositions of the present disclosure are designed to interact with and sequester micelles, such as those formed in the small intestine during the digestion process. Accordingly, the polymer compositions of the present disclosure may be referred to as micelle sequestrant polymers or MSPs. Micelles are complexes generally formed of triglycerides, bile acids, and in some instances cholesterol. As a result of the interaction with the micelle, the MSP prevents the micelle from absorbing in the digestive tract resulting in elimination of the micelle:MSP complex in the fecal matter of the organism.

MSPs may therefore be used to treat obesity and other related metabolic conditions and offer several advantages. First, MSPs may be formulated for convenient oral dosing. Second, they are not absorbed by the digestive tract resulting in fewer side effects as compared to other therapies, which increases long-term patient compliance. Finally, MSPs also allow for simultaneous treatment of hypercholesterolemia, elevated triglycerides, and weight gain, and therefore reduce the risk of adverse drug interactions and pharmacotherapy load.

In general, the MSPs of the present disclosure are copolymers comprising a pH-sensitive monomer and at least one positively-charged amine monomer. The pH-sensitive monomer is selected, at least in part, based on the pH in which it precipitates out of solution (a property related to monomer pKa). As used herein, the term "pH sensitive monomer" is a monomer which is hydrophilic (or water soluble) below the pH transition point and hydrophobic (or water insoluble) above the pH transition point. Whereas the positively-charged monomer is selected to retain its positive charge regardless of pH thereby permitting it to bind the negatively-charged micelle under most physiological environments in the digestive system. As used herein, the term "positively charged monomer" is a monomer containing positive-charged groups, and also the positive charge will not change (became neutral or negative) as pH changes within the ranges found in the gastrointestinal system. However, a MSP comprising a polymer of only pH-sensitive monomers, while possessing the ability to bind micelles at pH values lower than the transition point (due to its cationic state), does not flocculate well after the pH transition and displays a low sequestration efficiency. A MSP comprising a polymer of only positively-charged monomers will likely bind micelles, but will likely fail to induce flocculation of the complex since it will not precipitate at most pH values encountered in the digestive tract.

In one instance, the ability of a MSP to form a complex with a micelle and induce flocculation thereof can be expressed as a micelle sequestration efficiency. The term "micelle sequestration efficiency" as used herein and in the appended claims means the percentage of the starting micelle concentration or the components thereof (e.g. triglyceride, cholesterol, bile acid, etc) of a sample that is present in a polymer:micelle flocculent. Generally, the micelle sequestration efficiency is determined by the following procedure. A micelle containing fluid sample comprising, for example, a lipid and bile acid content sufficient to form micelles, is prepared. The MSP is added to the sample and the pH is adjusted to the transition point of the MSP thereby causing a flocculent to form. The flocculent is isolated and removed from the sample and the micelle components are measured in the remaining supernatant. Based on this measure, the percentage of measured micelle component no longer present in the sample following removal of the flocculent provides the micelle sequestration efficiency. The examples provided herein describe various methods for measuring the micelle sequestration efficiency in further detail.

In one embodiment, the micelle sequestration efficiency is measured by the Micelle Sequestration Assay I. As used herein and in the appended claims, the term "Micelle Sequestration Assay I" is performed as follows. A bile acid stock solution is used which contains four primary bile acids, which make up about 80% of total human bile acid content: glycocholic acid (GC), glycochenodeoxycholic acid (GCDC), taurocholic acid (TC), and taurochenodeoxycholic acid (TCDC). The bile acid stock solution (1% wt) is prepared in simulated intestinal fluid with a mass ratio of 4:2:2:1 (GC:GCDC:TC:TCDC, respectively) according to human bile acid composition. A micelle stock solution is prepared by adding 200 ul of glyceryl trioleate (triglyceride) to 10 mL of a bile acid stock solution. The glyceryl trioleate is suspended by vortexing vigorously followed by sonication (20 sec). The resulting solution was vigorously stirred over night to form the final fat micelle stock solution. For the fat micelle sequestration assay, the micelle sequestration polymer is initially mixed with the fat micelle stock solution at different polymer/bile acids ratios (e.g., 0.25×, 0.5×, and 1×). NaOH solution is then added to increase the pH value above the pH transition point to drive precipitation of polymer/micelle complexes. The supernatant of the solution following removal of the precipitated polymer/micelle complex is analyzed by HPLC or a triglyceride assay kit to quantify the residual triglyceride concentrations or other components of the micelle including bile acid concentrations thereby providing the percentage of starting micelle concentration that was precipitated or flocculated (i.e., sequestered) by each polymer (sequestration efficiency). Bile acid sequestration capacity represents the quantity (mg) of bile acid sequestered per quantity (mg) of polymer.

In another embodiment, the micelle sequestration efficiency is measured by the Micelle Sequestration Assay II. As used herein and in the appended claims, the term "Micelle Sequestration Assay II" is performed as follows. A micelle stock solution containing glyceryl trioleate and cholesterol is prepared by dissolving 6 mg of cholesterol in 200 µl of glycercyl trioleate and then transferring this mixture into 10 ml of the bile acid stock solution described in the Micelle Sequestration Assay I. The oil phase (glyceryl trioleate and cholesterol) was suspended by vigorous vortex and sonication for 20 seconds. The formed milk-like solution was vigorously stirred over night to form the final fat micelle stock solution (micelle solution).

Polymer (for which you are testing micelle sequestration efficiency) is added to the micelle solution at a polymer/bile acids (of the micelle solution) ratio of 0.5×. NaOH solution is then added to the micelle solution to increase the pH value of the solution to at least 8 and the solution is mixed by vortexing thereby inducing flocculation of any formed micelle:polymer complex. The flocculent-containing pellet is collected via centrifugation at 1000 rpm for 2 min. The supernatant is collected and removed from the flocculent pellet. Fresh simulated intestinal fluid without bile acid, triglyceride, and cholesterol (pellet wash buffer) is then added to the flocculent-containing pellets and left therein for eight hours. Eight hours later, the sample containing flocculent pellet and pellet wash buffer is then centrifuged and the supernatant (Wash Supernatant) is collected, and the remaining flocculent-containing pellets are dissolved in 10% Triton X-100 in isopropanol by vigorous vortexing and alternating sonication for 20 seconds until the pellet is fully dissolved (approximately 10 minutes). Levels of triglyceride and cholesterol are then measured (by any commercially available kit designed to measure such) in the starting micelle solution (to give starting concentrations), in the supernatant (to determine the percentage of starting concentrations remaining or not sequestered—indirect measure of sequestration efficiency), in the wash supernatant (to determine if any micelles or micelle constituents are diluted out of the polymer complex), and in the solubilized flocculent-containing pellets (for a direct measurement of sequestration).

In one instance, the polymer compositions of the present disclosure comprise a micelle sequestration efficiency from about 50% to about 100% and more preferably from about 85% to 100%.

As discussed above, the pH-sensitive monomer provides the ability of the polymer composition to precipitate at a particular pH. In certain embodiments, the pH-sensitive monomer has a pKa from about 4.0 to about 9.5. In other embodiments, the pH-sensitive monomer has a pKa from about 5.0 to about 8.5 and from about 6.0 to about 7.0. For example, an MSP comprising a pH-sensitive monomer having a pKa of 6.9 (referring to the conjugate acid) and a positively-charged monomer may form a complex with negatively-charged micelles in the small intestine at a pH of 5, and upon reaching an environment where the pH is at or above 6.9, induces flocculation of the micelle complex thereby preventing absorption of the micelle in the digestive tract. It should be understood however that when the pH-sensitive monomer is co-polymerized with the positively-charged monomer, the pH at which the polymer composition precipitates may not be the pKa of the pH-sensitive monomer. Instead, the amount or ratio of the positively-charged monomer to pH-sensitive monomer may offset the pH transition point of the copolymer from the pKa of its constituent pH-sensitive monomer. For example, the pKa of the polymer is lower than the pKa of its constituent pH-sensitive monomer.

Suitable pH-sensitive monomers comprise an amine, for example, a tertiary amine. Examples of pH-sensitive monomers include, but are not limited to 2-vinylpyridine (VP), 2-(Diethylamino)ethyl methacrylate (DEA), 2-(dibutylamino)ethyl methacrylate (DBA), and 2-(diisopropylamino)ethyl methacrylate (DPA).

The positively-charged monomer maintains its charge throughout most pH ranges and provides the ability of the polymer composition to complex with the negatively-charged micelles. In one embodiment, a suitable positively-charged monomer comprises a salt, for example, an ammonium cation. Moreover, a positively-charged monomer may comprise a tertiary or quaternary ammonium cation. Further examples of suitable positively-charged monomers include, but are not limited to (Vinylbenzyl)trimethylammonium chloride (VBA), 2-[(Methacryloyloxy)ethyl]trimethylammonium chloride (MAM) and diallyldimethylammonium chloride (DAM).

The present polymer composition may therefore include one or more of the pH-sensitive monomers disclosed herein copolymerized with one or more of the positively-charged monomers described herein. For example, the polymer composition of the present disclosure may include: a copolymer of one or more of the group consisting of VP, DPA, DBA, and DEA and one or more of the group consisting of VBA, MAM, and DAM; a copolymer of DBA and one or more of VBA, MAM and DAM; a copolymer of DPA and one or more of VBA, MAM and DAM; a copolymer of DEA and one or more of VBA, MAM and DAM; a copolymer of VP and one or more of VBA, MAM and DAM; a copolymer of DBA, a second pH sensitive monomer, and one or more of VBA, MAM and DAM; a copolymer of DPA, a second pH sensitive monomer, and one or more of VBA, MAM and DAM; a copolymer of DEA, a second pH sensitive monomer, and one or more of VBA, MAM and DAM; a copolymer of VP, a second pH sensitive monomer, and one or more of VBA, MAM and DAM; a copolymer of DBA and MAM or PDBA-PMAM; a co-polymer of DBA and VBA or PDBA-PVBA; a co-polymer of DBA, MAM, and VBA or PDBA-PMAM-PVBA; a co-polymer of DPA and MAM or PDPA-PMAM; a co-polymer of DPA, MAM and VBA or PDPA-PMAM-PVBA; and a copolymer of DPA and VBA or PDPA-PVBA. It should be understood however that there may be other monomers not disclosed herein that possess the properties associated with a pH-sensitive monomer and positively-charged monomer and such monomers would be identifiable by one of ordinary skill in the art based on the present disclosure.

Generally, the ratio of pH-sensitive monomer to positively charged monomer in the polymer compositions of the present disclosure may vary widely based on each type of monomer utilized in the resulting polymer. In one embodiment, the polymer compositions of the present disclosure comprise a co-polymer of a pH-sensitive monomer and of a positively-charged monomer at a ratio of about 50:50 to about 90:10, respectively, or from about 51:49 to about 89:11, or from about 52:48 to about 88:12, or from about 53:47 to about 87:13, or from about 54:46 to about 86:14, or from about 55:45 to about 85:15, or from about 56:44 to about 84:16, or from about 57:43 to about 83:17, or from about 58:42 to about 82:18, or from about 59:41 to about 81:19, or from about 60:40 to about 80:20, or from about 61:39 to about 79:21, or from about 62:38 to about 78:22, or from about 63:37 to about 77:23, or from about 64:36 to about 76:24, or from about 65:35 to about 75:25, or from about 66:34 to about 74:26, or from about 67:33 to about 73:27, or from about 68:32 to about 72:28, or from about 69:31 to about 71:29, or preferably about 70:30, respectively. It should be understood that these ratios may comprise a copolymer of one or more pH-sensitive monomers and one or more positively charged monomers so long as the total for each class of monomer (pH-sensitive and positively-charged) is present at the listed ratio regardless of the number of different monomer species included in each class. For example, a ratio of pH-sensitive monomer to positively charged monomer of 70:30 may comprise a single pH-sensitive monomer and two positively charged monomers at a ratio of 70:20:10 or 70:15:15. For any of the above listed ratios, the polymer composition of the present disclosure may include the following: a copolymer of a pH-sensitive monomer selected from the group consisting of VP, DPA, DBA, and DEA and one or more positively charged monomers selected from the group consisting of VBA, MAM, and DAM; a copolymer of DBA and one or more of VBA, MAM and DAM; a copolymer of DPA and one or more of VBA, MAM and DAM; a copolymer of DEA and one or more of VBA, MAM and DAM; a copolymer of VP and one or more of VBA, MAM and DAM; a copolymer of one or more pH-sensitive monomers selected from the group consisting of VP, DPA, DBA, and DEA and one or more positively charged monomers selected from the group consisting of VBA, MAM, and DAM; a copolymer of DBA, a second pH sensitive monomer, and one or more of VBA, MAM and DAM; a copolymer of DPA, a second pH sensitive monomer, and one or more of VBA, MAM and DAM; a copolymer of DEA, a second pH sensitive monomer, and one or more of VBA, MAM and DAM; a copolymer of VP, a second pH sensitive monomer, and one or more of VBA, MAM and DAM; a copolymer of DBA and MAM or PDBA-PMAM; a co-polymer of DBA and VBA or PDBA-PVBA; a co-polymer of DBA, MAM, and VBA or PDBA-PMAM-PVBA; a co-polymer of DPA and MAM or PDPA-PMAM; a co-polymer of DPA, MAM and VBA or PDPA-PMAM-PVBA; and a copolymer of DPA and VBA or PDPA-PVBA.

In certain embodiments, the polymer compositions of the present disclosure are capable of forming a complex with a micelle under physiological conditions associated with the small intestine. In certain embodiments, the physiological conditions include a pH from about 4 to about 8. In other embodiments, the compositions described herein are capable of forming a complex with a micelle at a pH of from about 4.5 to about 7.5 and from about 5.0 to 7.0. In yet other embodiments, the compositions described herein are capable of forming a complex with a micelle at a pH of less than 6.0

In certain embodiments, upon forming a complex with a micelle, the polymer compositions of the present disclosure can be characterized by their ability to induce aggregation or flocculation of the MSP:micelle complex upon a change in pH beyond a certain value, for example, when the complex encounters a more basic environment in the small intestine. This value is generally related to the pKa of the pH-sensitive monomer of the polymer composition, but is influenced by the relative amount of positively-charged monomer present in the polymer composition. In certain embodiments, the polymer compositions may induce aggregation or flocculation of the MSP:micelle complex at a pH from about 4.0 to about 9.5, from about 5.0 to about 8.5, or from about 6.0 to about 7.0. In one instance, the present polymer compositions may be made by copolymerizing the pH-sensitive monomer and one or more positively-charged monomer in the presence of an initiator. After polymerization the MSP may be purified and lyophilized.

The polymer compositions of the present disclosure may form part of larger complexes that include other polymer or non-polymer components. In addition, the polymer compositions of the present disclosure may be packaged and provided for administration in a variety of different forms.

It should be understood that the polymer compositions described herein and in the appended claims can include multiple repeats of each monomer provided and should not be limited to a composition comprising a single unit of each named monomer. The Examples provided herein below provide a more detailed explanation of one manner to generate various example MSPs of the present disclosure.

An noted above, the MSPs of the present disclosure may be formulated into a dosage form suitable for oral delivery such as, for example, tablet, capsule, suspension, and the like.

Methods of using the present polymer compositions are also provided. In certain embodiments, the method comprises administering a polymer composition of the present disclosure to an animal or human. The route of administration is generally oral, but may include other delivery methods that provide the polymer composition to the stomach. In certain embodiments, the polymer composition is administered to an animal or human with the consumption of food, particularly food high in dietary fats.

In certain embodiments, the present polymer compositions are administered to animals or humans to treat various metabolic-related conditions. For example, the present polymer compositions are administered to animals or humans having elevated triglycerides, elevated cholesterol, or to promote weight loss. In other embodiments, the present polymer compositions are administered to animals or humans having multiple conditions including elevated cholesterol, elevated triglycerides and obesity.

Figure 1:
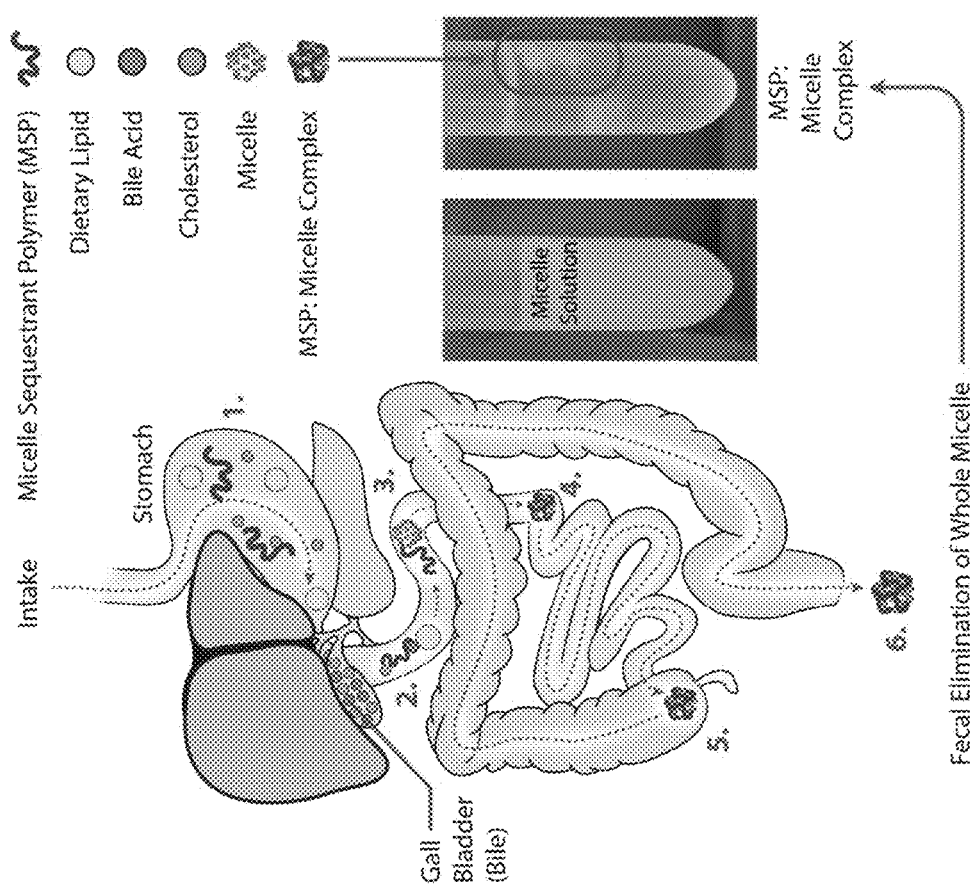
FIG. 1 provides a potential mechanism of action of the present polymer compositions to sequester micelles in the gastrointestinal tract.

In order to further illustrate the potential benefits of the present polymer compositions, FIG. 1 provides an overview of a potential mechanism of action of the present polymer compositions. However, it should be understood that the present compositions and methods should not be limited by this particular mechanism of action and may be acting to produce its effects by other mechanisms alone or in concert with the mechanism described herein. In this instance and referring now to FIG. 1, the polymer composition is administered orally and enters the stomach where it mixes with the food content therein as indicated at "1." It should be noted that in this mechanism, the polymer composition is soluble in the acidic environment of the stomach. As indicated at "2," chyme containing the MSP enters the duodenum stimulating gall bladder contraction and bile is released into the small intestine where bile acids, cholesterol, and lipids form micelles. At "3," the MSPs bind whole micelles via charge:charge interaction of the MSP and the bile acid component of the micelle, while the pH change of the small intestine (~pH 5.5-8.0) causes the MSPs to aggregate and form stable MSP:micelle complexes, which flocculate out of suspension (see exemplary pictoral representation of an aggregate comprising the MSP:micelle complex in right panel of FIG. 1). At "4" and "5" the stable complex progresses through the small intestine to the large intestine and is eliminated in the feces as shown at position "6."

To facilitate a better understanding of the present invention, the following examples of specific instances are given. In no way should the following examples be read to limit or define the entire scope of the invention.

EXAMPLES

Example 1

Synthesis of Poly(2-(Diisopropylamino)ethyl methacrylate hydrochloride-co-[2-(Methacryloyloxy) ethyl]trimethylammonium chloride) (PDPA-PMAM13)

DPA, 2.37 mL (10 mmol), MAM, 270 mg (1.3 mmol), and initiator, 2,2'-Azobis(2-methylpropionamidine) dihydrochloride (AAPH), 15 mg, were added into 15 mL of 1 M HCl solution. After DPA and MAM were totally dissolved, the solution was purged with nitrogen for 20 min. The vial was sealed and the polymerization was carried out in an oil bath at 70° C. for 24 h. Then the polymerized solution was transferred into a dialysis bag (MWCO 3400) to remove unreacted monomers, initiator and hydrochloric acid. After 3 days of dialysis, the purified polymer was obtained via lyophilization.

Figure 2:
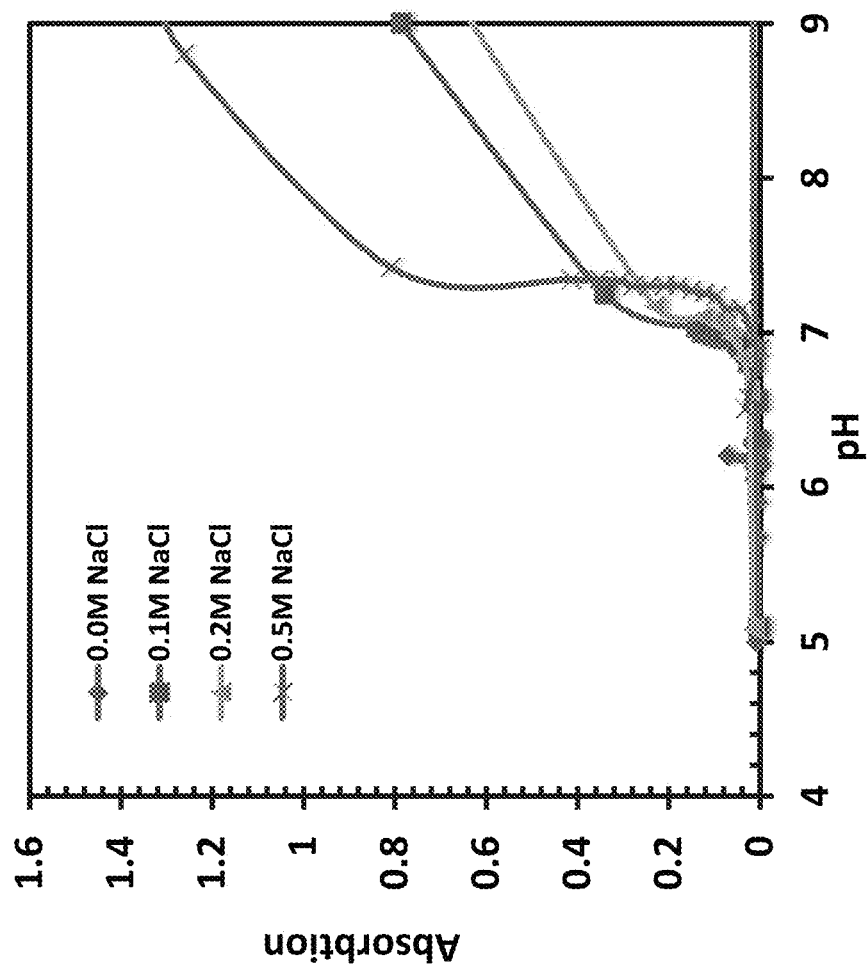
FIG. 2 represents the absorbance of PDPA-PMAM13 at various NaCl concentrations with increasing pH.

Referring now to FIG. 2, the pH transition point for the present polymer was determined in various NaCl solution (0, 0.1, 0.2, 0.5 M) with a polymer concentration of 1 mg/mL. The pH values were adjusted by NaOH (0.1 M) and HCl (0.1 M) solution, and the absorbances of the polymer solution at various concentrations were determined at 500 nm by the UV/vis spectrophotometer. Using this method, the pH transition point for PDPA-PMAM13 is about 7.0 as shown in FIG. 2.

Example 2

Synthesis of Poly(2-(Dibutylamino)ethyl methacrylate hydrochloride-co-[2-(Methacryloyloxy ethyl] trimethylammonium chloride) (PDBA-PMAM19)

DBA, 2.65 mL (10 mmol), MAM, 394.7 mg (1.9 mmol), and initiator AAPH, 15 mg were added into 15 mL of 1 M HCl solution. After DBA and MAM were totally dissolved, the solution was purged with nitrogen for 20 min. The vial was sealed and the polymerization was carried out in an oil bath at 70° C. for 24 h. Then the polymerized solution was transferred into a dialysis bag (MWCO 3400) to remove unreacted monomers, initiator and hydrochloric acid. After 3 days of dialysis, the purified polymer was obtained via lyophilization.

Figure 3:
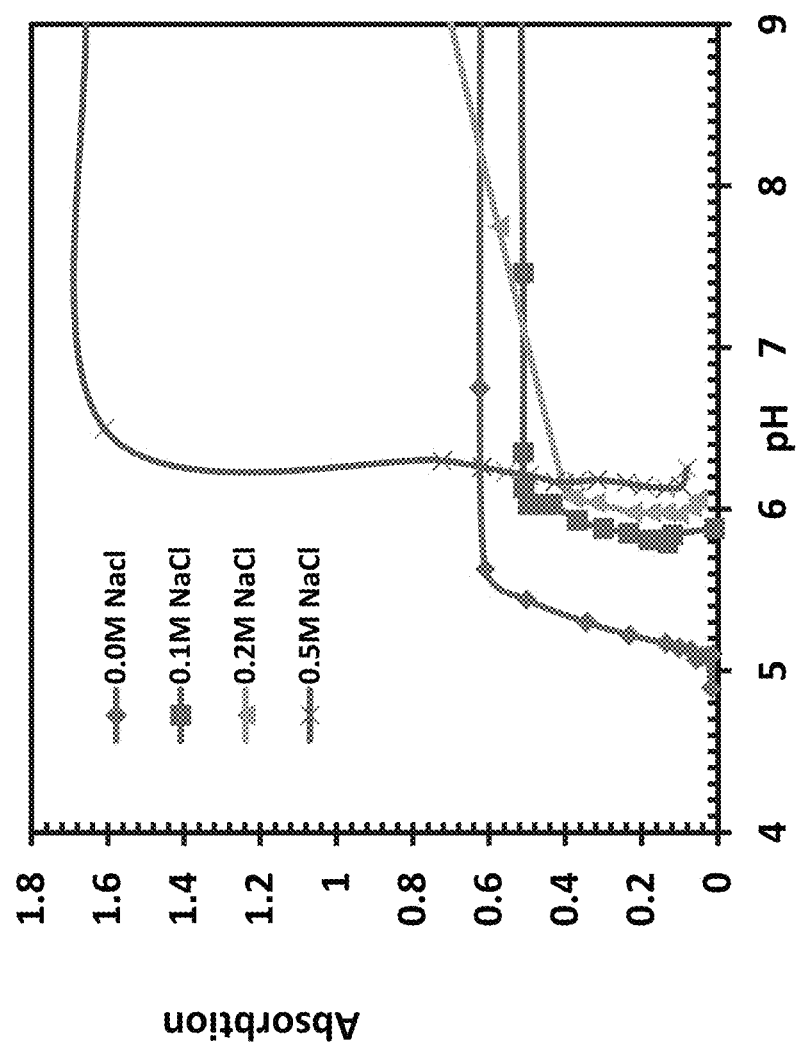
FIG. 3 represents the absorbance of PDBA-PMAM19 at various NaCl concentrations with increasing pH.

Referring now to FIG. 3, using the method described above, the pH transition point for PDBA-PMAM19 was determined to be about 6.0.

Example 3

Synthesis of Poly(2-(Diisopropylamino)ethyl methacrylate hydrochloride-co-(Vinylbenzyl)trimethylammonium chloride) (PDPA-PVBA16)

DPA, 2.37 mL (10 mmol), VBA, 338.7 mg (1.6 mmol), and initiator AAPH, 15 mg, were added into 15 mL of 1 M HCl solution. After DPA and VBA were totally dissolved, the solution was purged with nitrogen for 20 min. The vial was sealed and the polymerization was carried out in an oil bath at 70° C. for 24 h. Then the polymerized solution was transferred into a dialysis bag (MWCO 3400) to remove unreacted monomers, initiator and hydrochloric acid. After 3 days of dialysis, the purified polymer was obtained via lyophilization. Using the method described in Example 1, the pH transition point for PDPA-PVBA16 was determined to be about 7.0.

Example 4

Synthesis of Poly(2-(Dibutylamino)ethyl methacrylate hydrochloride-co-(Vinylbenzyl)trimethylammonium chloride) (PDBA-PVBA20)

DBA, 2.65 mL (10 mmol), VBA, 423.4 mg (2 mmol), and initiator AAPH, 15 mg, were added into 15 mL of 1 M HCl solution. After DBA and VBA were totally dissolved, the solution was purged with nitrogen for 20 min. The vial was sealed and the polymerization was carried out in an oil bath at 70° C. for 24 h. Then the polymerized solution was transferred into a dialysis bag (MWCO 3400) to remove unreacted monomers, initiator and hydrochloric acid. After 3 days of dialysis, the purified polymer was obtained via lyophilization. Using the method described in Example 1, the pH transition point for PDBA-PVBA20 was determined to be about 6.0.

Example 5

Synthesis of Poly(2-(Diisopropylamino)ethyl methacrylate hydrochloride-co-[2-(Methacryloyloxy) ethyl]trimethylammonium chloride-co-(Vinylbenzyl) trimethylammonium chloride) (PDPA-PMAM4-PVBA18)

Figure 4:
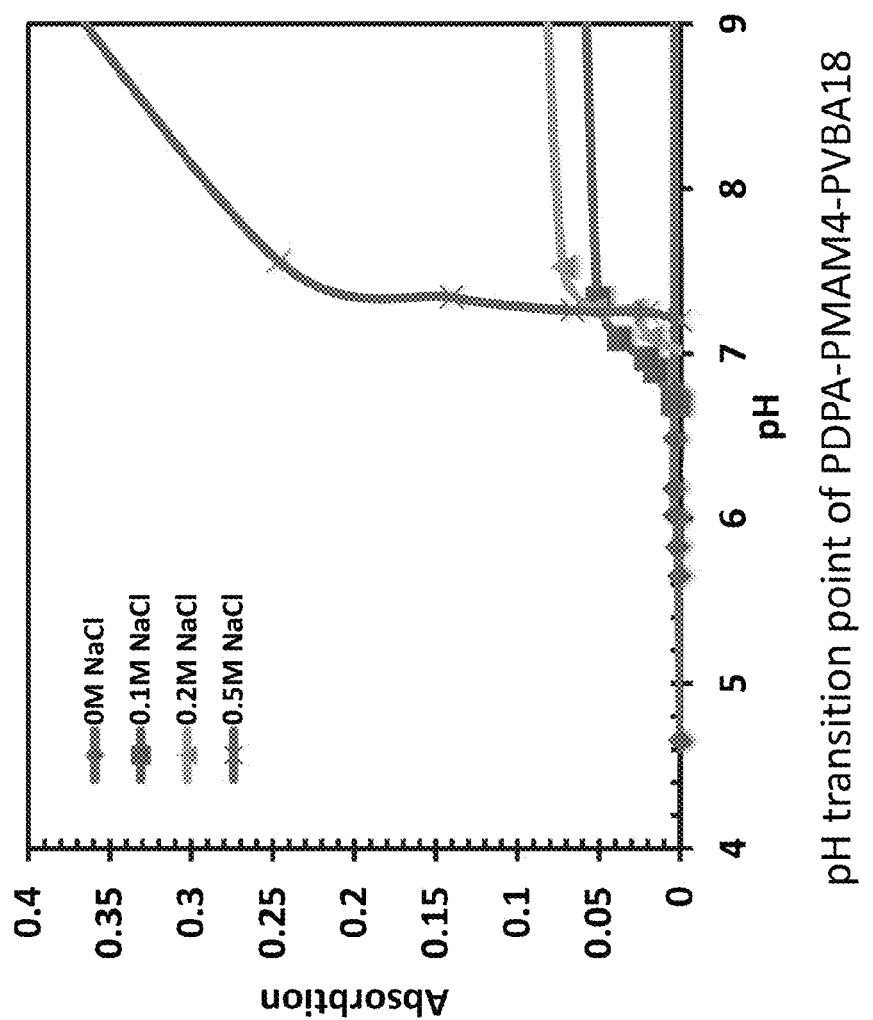
FIG. 4 represents the absorbance of PDPA-PMAM4-PVBA18 at various NaCl concentrations with increasing pH.

DPA, 2.37 mL (10 mmol), MAM, 83.1 mg (0.4 mmol), VBA, 381 mg (1.8 mmol), and initiator AAPH, 15 mg, were added into 15 mL of 1 M HCl solution. After all the monomers were totally dissolved, the solution was purged with nitrogen for 20 min. The vial was sealed and the polymerization was carried out in an oil bath at 70° C. for 24 h. Then the polymerized solution was transferred into a dialysis bag (MWCO 3400) to remove unreacted monomers, initiator and hydrochloric acid. After 3 days of dialysis, the purified polymer was obtained via lyophilization. Referring now to FIG. 4, monomers were totally dissolved, the solution was purged with nitrogen for 20 min, the vial was sealed and the polymerization was carried out in an oil bath at 70° C. for 24 h. Then the polymerized solution was transferred into a dialysis bag (MWCO 3400) to remove unreacted monomers, initiator and hydrochloric acid. After 3 days of dialysis, the purified polymer was obtained via lyophilization. Using the method described in Example 1, the pH transition point for PDBA-PMAM10-PVBA20 was determined to be about 6.0.

Example 6

Synthesis of Poly(2-(Dibutylamino)ethyl methacrylate hydrochloride-co-[2-(Methacryloyloxy)ethyl] trimethylammonium (Diallyldiethylammonium chloride) (PDBA-PMAM4-PDAM20)

DBA, 2.65 mL (10 mmol), MAM, 83.1 mg (0.4 mmol), DAM, 323.4 mg (2 mmol), and initiator AAPH, 15 mg, were added into 15 mL of 1 M HCl solution. After all the monomers were totally dissolved, the solution was purged with nitrogen for 20 min. The vial was sealed and the polymerization was carried out in an oil bath at 70° C. for 24 h. Then the polymerized solution was transferred into a dialysis bag (MWCO 3400) to remove unreacted monomers and initiator. After 3 days of dialysis, the purified polymer was obtained via lyophilization. The pH transition point of this polymer was determined to be about 6.0.

Example 7

Bile Acid Sequestration Efficiency

Four primary bile acids, glycocholic acid (GC), glycochenodeoxycholic acid (GCDC), taurocholic acid (TC), and taurochenodeoxycholic acid (TCDC), make up about 80% of total human bile acid content, and were used in the present assay. The bile acid stock solution (1% wt) was prepared in simulated intestinal fluid with a mass ratio of 4:2:2:1 (GC: GCDC:TC:TCDC, respectively) according to human bile acid composition.

For the bile acid sequestration assay, various polymer solutions, including exemplary polymers of the present disclosure as well as Cholestyramine (see x-axis of FIG. 5 for total list of polymers tested), were mixed with bile acid solution at various polymer:bile acid ratios (1×; 2×; 5×; 10×). Subsequently, NaOH solution was added to the mixture to increase the pH value of the solution above the pH transition point of the polymer to precipitate the bile acid/polymer complex. After 4 hours (to ensure all the loosely bound bile acids were release back to the solution), the supernatant of the solution was passed through a 0.22 μm filter and then analyzed by HPLC or a bile acid assay kit to quantify the residual bile acid concentration.

Figure 5:
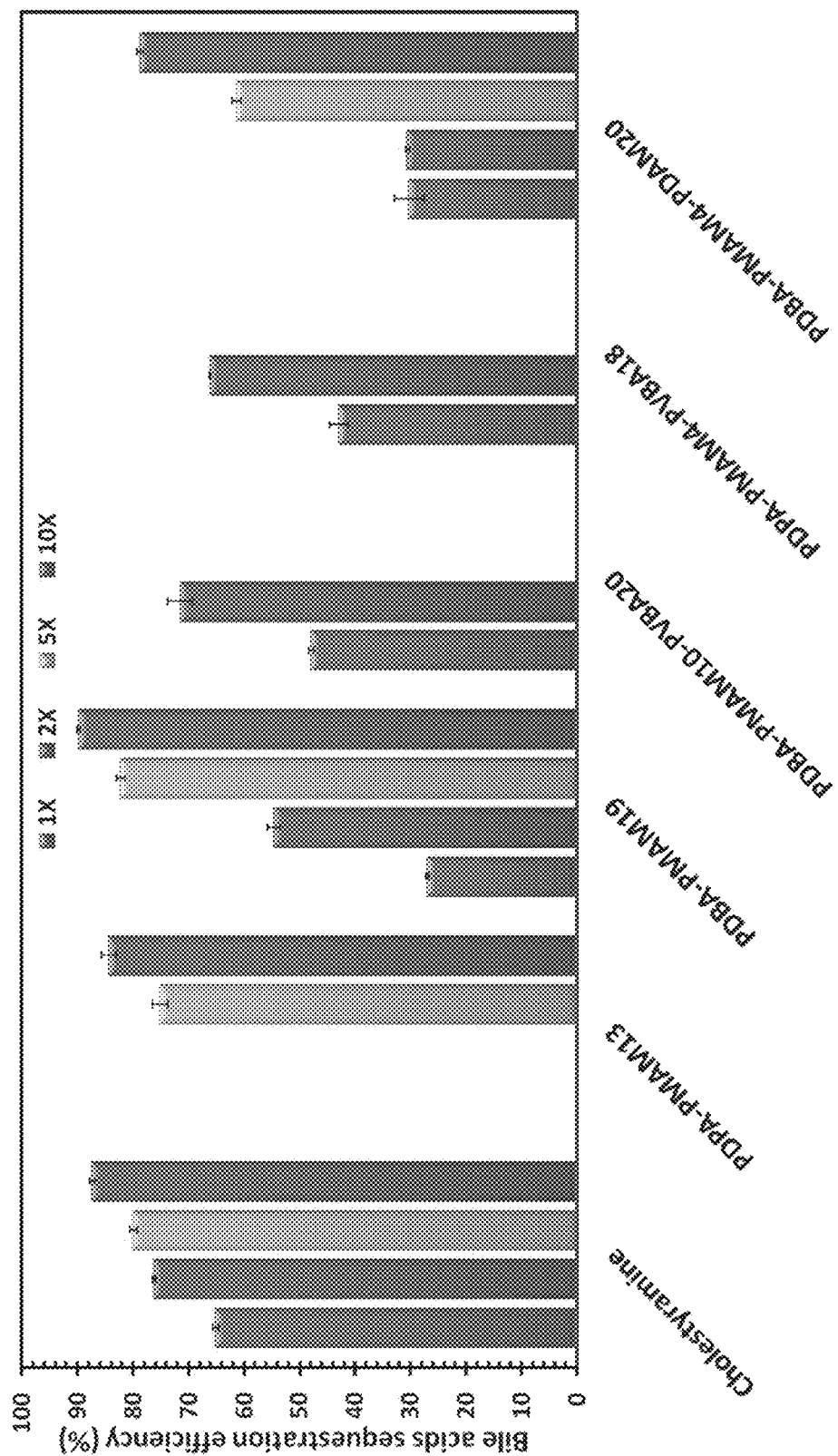
FIG. 5 provides a bar graph demonstrating the bile acid sequestration efficiency of Cholestyramine as compared to various polymer compositions of the present disclosure at polymer concentrations of 1× to 10× of bile acid concentration.
Figure 6:
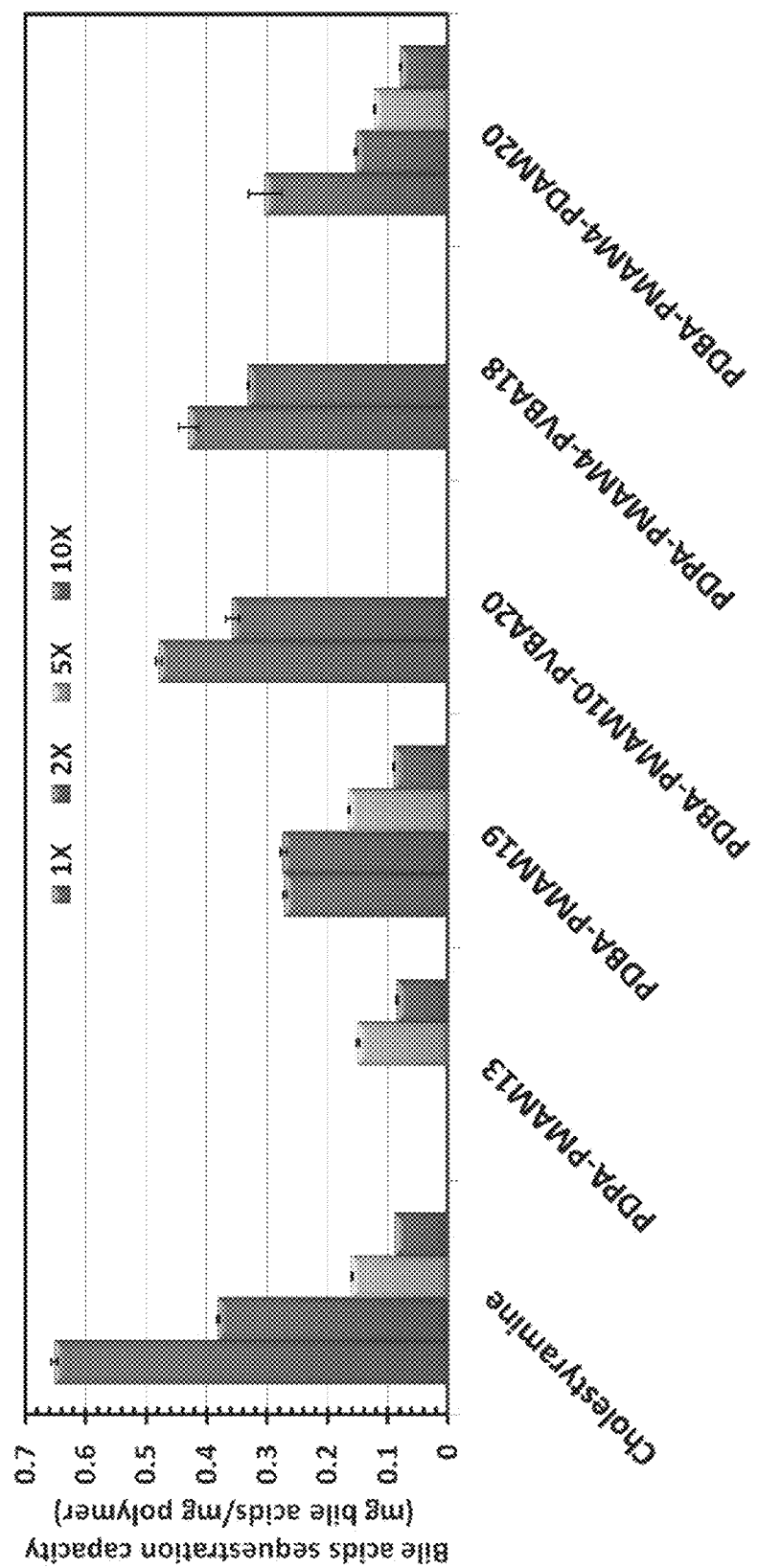
FIG. 6 provides a bar graph demonstrating the bile acid sequestration capacity of Cholestyramine as compared to various polymer compositions of the present disclosure at polymer concentrations of 1× to 10× of bile acid concentration.

The results are represented in FIGS. 5 and 6 as the bile acid sequestration efficiency and the bile acid sequestration capacity, respectively. The bile acid sequestration efficiency was determined by measuring the bile acid content of the supernatant following removal of the precipitated complex thereby providing the percentage of the starting bile acid concentration precipitated with the polymer. Bile acid sequestration capacity represents the quantity (mg) of bile acid sequestered per quantity (mg) of polymer.

As demonstrated in FIG. 5, sequestration efficiency increased as the MAM content of the polymer increased and as the polymer:bile acid ratio increased. FIG. 6 demonstrates that sequestration capacity decreases as the polymer:bile acid ratio increases.

Example 8

Fat Micelle Sequestration Analysis

Micelle stock solution was prepared by adding 200 ul of glyceryl trioleate to 10 mL of the bile acid stock solution described in the above Example. The glyceryl trioleate was suspended by vortexing vigorously followed by sonication (20 sec). The resulting solution was vigorously stirred over night to form the final fat micelle stock solution.

For the fat micelle sequestration assay, PDBA-PMAM19, PDPA-PMAM4-PVBA18, PDBA-PMAM10-PVBA20, and Cholestyramine solutions were each initially mixed with the micelle stock solution were at polymer/bile acids ratios of 0.25×, 0.5×, and 1×. NaOH solution was then added to each mixture to increase the pH value above the pH transition point to drive precipitation of the polymer/micelle complexes. The supernatant of the solution following removal of the precipitated polymer/micelle complex was analyzed by HPLC or a triglyceride assay kit to quantify the residual triglyceride concentrations thereby providing the percentage of starting micelle concentration that was precipitated (sequestered) by each polymer (sequestration efficiency).

Figure 7:
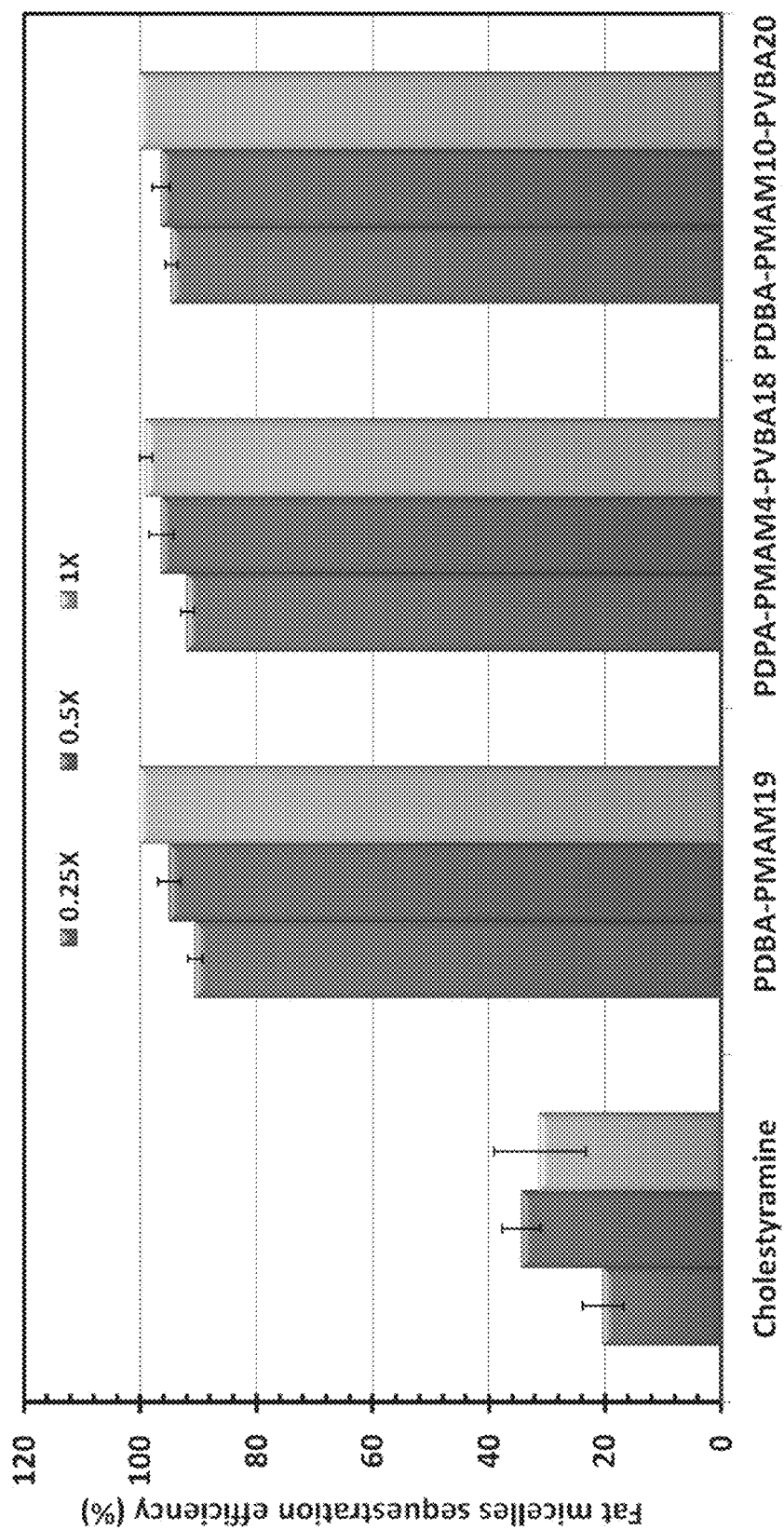
FIG. 7 provides a bar graph demonstrating the lipid/bile acid micelle (lipid/bile acid micelle) sequestration efficiency of Cholestyramine as compared to various polymer compositions of the present disclosure at polymer concentrations of 0.25× to 1× of lipid concentration.
Figure 8:
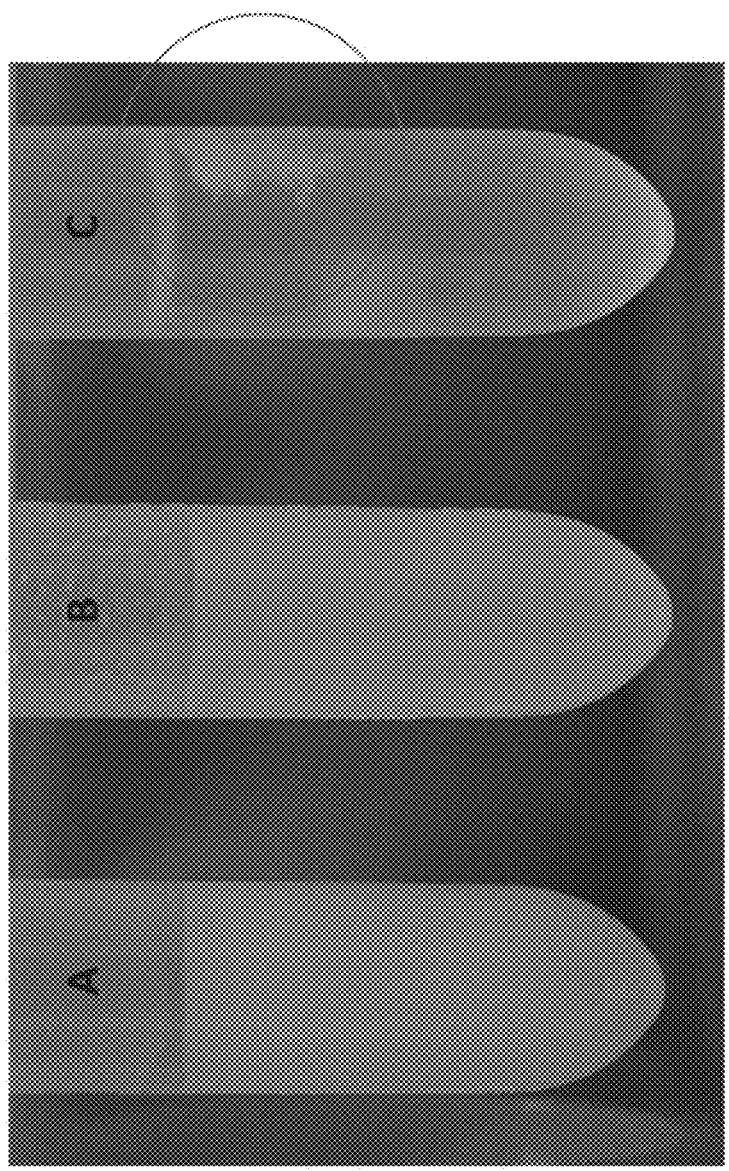
FIG. 8 is a pictorial representation of lipid/bile acid micelle flocculation in a micelle solution after pH changed to about 8.0 with (A) no polymer, (B) Cholestyramine, and (C) poly(2-(Dibutylamino)ethyl methacrylate hydrochloride-co-[2-(Methacryloyloxy)ethyl]trimethylammonium chloride) (PDBA-PMAM19).

As provided in FIG. 7, PDBA-PMAM19, PDPA-PMAM4-PVBA18 and PDBA-PMAM10-PVBA20 demonstrate a robust micelle sequestration efficiency as compared to Cholestyramine. Additionally, FIG. 8 provides a visual representation of micelle sequestration using another polymer of the present disclosure. As depicted, a milky aggregate was formed in tube C containing PDBA-PMAM19 which was absent in tube B containing Cholestyramine and tube A (vehicle control, $H_2O$).

Example 9

Weight Loss and Fecal Bile Acid Content is Increased in Mice Treated with Micelle Sequestrant Polymer

Materials and Methods

Mice were fed a standard chow diet (Harlan Teklad 2018) with approximately 6% kCal from fat and 18% kCal from protein. For the duration of study (5 days) mice were fasted overnight (~5:00 am-8:00 am). Mice were weighed every morning and administered either 300 mg/kg of polymer, 300 mg/kg Cholestyramine, or sterile H2O (Control) by oral gavage (10 ml/kg) at approximately 8:00 am prior to returning food and allowing ad libitum feeding until 5:00 PM. For high dose studies, mice were weighed every morning at approximately 8:00 am and were given 600 mg/kg polymer or Control (H2O; 10 ml/kg) by oral gavage and food was returned. At approximately 5:00 pm, mice were given a second dose of polymer (600 mg/kg) or Control (H2O; 10 ml/kg) to achieve a final dose of 1,200 mg/kg/day and then food was removed. In the present example, the polymer administered was poly(2-(Dibutylamino)ethyl methacrylate hydrochloride-co-[2-(Methacryloyloxy)ethyl]trimethylammonium chloride-co-(Vinylbenzyl)trimethylammonium chloride) (PDBA-PMAM10-PVBA20).

Fecal materials were collected daily, desiccated, weighed, and then pulverized in a mortar and pestle. Bile acids were extracted and saponified in 10 volumes 75% ethanol (i.e., 1 ml/100 mg dry feces) at 50° C. Fecal bile acids were determined by a commercially available enzymatic kit. Referring now to FIGS. 9A-9B, data is expressed as mean±S.D., n=4-6 mice per group. Statistical significance was determined at p<0.05 denoted by (*) as compared to once per day Control group (black bars) and denoted by (#) as compared to twice per day Control group (gray bars). For fecal bile acid analysis, data is expressed as mean, n=2 per group.

Results

As provided in FIGS. 9A-9B, weight loss was increased in mice treated with 300 mg/kg Cholestyramine, 300 mg/kg PDBA-PMAM10-PVBA20, and 1,200 mg/kg PDBA-PMAM10-PVBA20 with only the 300 mg/kg group (p=0.1) not reaching statistical significance by day 5. FIGS. 9C-9D demonstrate that fecal bile acids are increased in mice treated with 300 mg/kg Cholestyramine, 300 mg/kg PDBA-PMAM10-PVBA20, and 1,200 mg/kg PDBA-PMAM10-PVBA20. Thus, the MSP of PDBA-PMAM10-PVBA20 induces weight loss in a low fat diet and effectively sequesters bile acid and eliminates bile acid in feces.

Example 10

Colonic Bile Acids are Increased in Mice Treated with Micelle Sequestrant Polymer

Materials and Methods

Mice were fed a standard chow diet (Harlan Teklad 2018) with approximately 6% kCal from fat, 18% kCal from protein. Mice were fasted overnight (~5:00 am-8:00 am), weighed, and then given a single bolus dose of 1,500 mg/kg PDBA-PMAM10-PVBA20 or vehicle (H2O; 10 ml/kg) by oral gavage. Food was returned and mice were allowed to eat ad libitum. Mice were euthanized 6 hours later and small intestines and colon tissues were collected, snap frozen, and weighed. Small intestines and colons were homogenized and bile acids extracted and saponified in 10 volumes 75% ethanol at 50° C. Bile acid levels were determined by a commercially available enzymatic kit. Data is expressed as mean±S.D., n=3-4 mice per group. * Indicates statistical significance compared to vehicle ($H_2O$) gavage (p<0.05).

Results

Referring now to FIG. 10A, small intestinal bile acid levels were not significantly increased 6 hours after treatment with 1,500 mg/kg PDBA-PMAM10-PVBA20. However, as provided in FIG. 10B, colonic bile acid levels were significantly elevated 6 hours after treatment with 1,500 mg/kg PDBA-PMAM10-PVBA20. Thus, the MSP of PDBA-PMAM10-PVBA20 can effectively sequester bile acids and cause increased levels of bile acids in the colons of mice in a low fat diet.

Example 11

High Fat Diet-Induced Fecal Triglycerides and Weight Loss is Increased in Mice Treated PDBA-PMAM10-PVBA20

Materials and Methods

Mice were fed a high fat 'Western' diet (Harlan TD.08811; 45% kcal from milk fat, 30% kcal from sucrose) for 3 days prior to the initiation of the study protocol to get accustom to the diet. For the duration of study (5 days) mice were fasted overnight (~5:00 am-8:00 am). Mice were weighed every morning and administered either 300 mg/kg of polymer, 300 mg/kg Cholestyramine, or sterile H2O (Control) by oral gavage (10 ml/kg) at approximately 8:00 am prior to returning food and allowing ad libitum feeding until 5:00 PM. For high dose studies, mice were weighed every morning at approximately 8:00 am and were given 750 mg/kg polymer or Control (H2O; 10 ml/kg) by oral gavage and food was returned. At approximately 5:00 pm, mice were given a second dose of polymer (750 mg/kg) or Control (H2O; 10 ml/kg) to achieve a final dose of 1,500 mg/kg/day and then food was removed.

Fecal materials were collected, desiccated, weighed and pulverized with a mortar and pestle. Fecal bile acids were extracted and saponified in 10 volumes 75% ethanol at 50° C. and bile acid levels determined by a commercially available enzymatic kit. A Folch extraction was performed on 100 mg desiccated fecal powder for the isolation of fecal lipids; then fecal triglyceride levels were determined using a commercially available enzymatic kit. Referring now to FIGS. 11A-11D, data is expressed as mean±S.D., n=5-7 mice per group or n=4 cages per group (fecal triglyceride analysis). B) Statistical significance was determined at p<0.05 denoted by (*) as compared to once per day Control group (black bars), denoted by (#) as compared to twice per day Control group (gray bars). C-D) Statistical significance was determined at p<0.05 denoted by (*) as compared to once per day Control group (open bars), denoted by (#) as compared to Cholestyramine.

Results

As shown in FIGS. 11A-11B, weight loss was increased in mice treated with 300 mg/kg PDBA-PMAM10-PVBA20, and 1,500 mg/kg PDBA-PMAM10-PVBA20 as compared to corresponding control ($H_2O$) mice; however, the 300 mg/kg PDBA-PMAM10-PVBA20 group did not reach the level of statistical significance (p=0.1189). Additionally, mice treated with 1,500 mg/kg PDBA-PMAM10-PVBA20 displayed a significant increase in percent weight loss as compared to mice treated with 300 mg/kg Cholestyramine. Referring now to FIGS. 11C-11D, elimination of fecal bile acids were increased in both 300 mg/kg cholestyramine and PDBA-PMAM10-PVBA20 groups. Fecal concentrations of triglycerides were increased in mice fed a high fat diet containing 0.5% PDBA-PMAM10-PVBA20 compared to control (high fat diet) and mice fed a high fat diet containing 0.5% Cholestyramine.

Example 12

Consumption of High Fat Diet Containing MSP (PDBA-PMAM10-PVBA20) Enhances MSP-Induced Increase in Fecal Triglycerides Methods In this Example, the MSP (PDBA-PMAM10-PVBA20) or Cholestyramine was integrated into the high fat diet rather than being administered separately as in the above Example. Specifically, mice were fed a high fat 'Western' diet (Harlan TD.08811; 45% kcal from milk fat, 30% kcal from sucrose) for 3 days prior to the initiation of the study protocol to acclimate to the diet. Mice were then given control (western) high fat diet, high fat diet containing 0.5% cholestyramine, or high fat diet containing 0.5% PDBA-PMAM10-PVBA20 for 72 hours.

Fecal materials were collected, desiccated, weighed and pulverized with a mortar and pestle. Fecal bile acids were extracted and saponified in 10 volumes 75% ethanol at 50° C. and bile acid levels determined by a commercially available enzymatic kit. A Folch extraction was performed on 100 mg desiccated fecal powder for the isolation of fecal lipids and triglycerides were determined using a commercially available enzymatic kit. Referring now to FIGS. 12A-12B, data is expressed as mean±S.D., n=4-5 mice per group. Statistical significance was determined at p<0.05 denoted by (*) as compared to control high fat diet (open bars), denoted by (#) as compared to Cholestyramine.

Results

As shown in FIGS. 12A-12B, the concentration of bile acids were increased in both mice fed a high fat diet containing 0.5% Cholestyramine or a high fat diet containing 0.5% PDBA-PMAM10-PVBA20 compared to control (high fat diet). Fecal concentrations of triglycerides were increased in mice fed a high fat diet containing 0.5% PDBA-PMAM10-PVBA20 compared to control (high fat diet) and mice fed a high fat diet containing 0.5% Cholestyramine.

Thus, the MSP of PDBA-PMAM10-PVBA20 can effectively sequester and increase fecal elimination of bile acids and triglycerides in mice on a high fat diet and can induce weight loss in mice on a high fat diet.

Example 13

Ability of PDBA-PMAM10-PVBA20 to Sequester Triglycerides and Cholesterol in a Simulated GI Fluid Sample Methods To prepare micelles stock solution containing glyceryl trioleate and cholesterol, 6 mg cholesterol was first dissolved in 200 ul of glyceryl trioleate (triglyceride), then this mixture was transferred into 10 ml of bile acid stock solution. The oil phase (glyceryl trioleate and cholesterol) was suspended by vigorous vortex and sonication for 20 seconds. The formed milk-like solution was vigorously stirred over night to form the final fat micelles stock solution.

To sequester micelles, polymer was added to the micelle solution and were mixed with a polymer/bile acids ratio of 0.5×. To flocculate whole micellsmicelles (and polymer) NaOH solution was added to the above solution to increase the pH value of the solution to 8.0, and the solution was mixed by vortexing. (Micelle Solution). The flocculated pellets were collected via centrifugation at 1000 rpm for 2 min. The supernatant of the solution(s) were collected (Supernatant) and then fresh simulated intestinal fluid (without micelles) was added to the collected pellets to wash the pellets. Eight hours later, the samples were centrifuged, supernatants (washWash Supernatant) were collected, and the pellets were dissolved in 10% Triton-X 100 in isopropanol via by vigorous vortexing and sonication for 20 seconds. (Solubilized Pellet).

Results

Referring now to FIGS. 13A and 13B, levels of triglyceride (13A) and cholesterol (13B) were determined in stock micelle solution (baseline; black bars), supernatants of micelle:polymer solution after flocculation at pH 8.0 (Supernatant), wash supernatants, and solubilized pellets by commercially available enzymatic assay kits.

The data provided in FIGS. 13A and 13B suggest that MSPs flocculate ~90% of triglyceride and cholesterol from micelles in stimulated GI-fluid and that flocculated micelle:polymer complexes are stable, as no detectable levels of triglycerides or cholesterol was present in the pellet washing buffer (GI-fluid without micelles). Furthermore, triglycerides and cholesterol are recovered in the solubilized pellet flocculum.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

The use of the word "a" or "an" when used in conjunction with the term "comprising" in the claims and/or the specification may mean "one," but it is also consistent with the meaning of "one or more," "at least one," and "one or more than one." As used herein "another" may mean at least a second or more.

It is contemplated that any instance or embodiment discussed in this specification can be implemented with respect to any method or composition of the invention, and vice versa. Furthermore, compositions of the invention can be used to achieve the methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A composition comprising:
a copolymer comprising a pH-sensitive monomer selected from the group consisting of 2-vinylpyridine, 2-(diethylamino)ethyl methacrylate, 2-(dibutylamino)ethyl methacrylate, and 2-(diisopropylamino)ethyl methacrylate and one or more of a positively-charged monomer selected from the group consisting of (vinylbenzyl)trimethylammonium chloride and [2-(methacryloyloxy)ethyl]trimethylammonium chloride; the ratio of pH-sensitive monomer to the one or more positively-charged monomer is about 50:50 to about 90:10, respectively; and the copolymer is in a soluble phase below a transition point and in an insoluble phase above the transition point, and wherein the transition point falls within a pH range from about 4.0 to about 9.5.

2. The composition of claim 1 wherein the copolymer further comprises a second positively-charged monomer.

3. The composition of claim 2 wherein one positively-charged monomer is [2-(methacryloyloxy)ethyl]trimethylammonium chloride and the second positively-charged monomer is (vinylbenzyl)trimethylammonium chloride.

4. The composition of claim 1 wherein the pH-sensitive monomer is 2-(dibutylamino)ethyl methacrylate and the positively-charged monomer is [2-(methacryloyloxy)ethyl]trimethylammonium chloride.

5. The composition of claim 4 wherein the copolymer further comprises an additional positively-charged monomer, wherein the additional positively-charged monomer is (vinylbenzyl)trimethylammonium chloride.

6. The composition of claim 5 wherein the ratio of 2-(dibutylamino)ethyl methacrylate to [2-(methacryloyloxy)ethyl]trimethylammonium chloride to (vinylbenzyl)trimethylammonium chloride is about 66:12:22.

7. The composition of claim 1 wherein the copolymer comprises (vinylbenzyl)trimethylammonium chloride and an additional positively-charged monomer, wherein the additional positively-charged monomer is diallyldimethylammonium chloride.

8. The composition of claim 1 further comprising a lipid micelle bound to the copolymer.

9. The method of claim 1 wherein the transition point falls within a pH range from about 5.0 to about 8.5.

10. The method of claim 1 wherein the transition point falls within a pH range from about 6.0 to about 7.0.

11. A method for treating a metabolic disorder comprising administering to a subject suffering from the metabolic disorder a composition comprising a copolymer, wherein the copolymer comprises a pH-sensitive monomer selected from the group consisting of 2-vinylpyridine, 2-(diethylamino)ethyl methacrylate, 2-(dibutylamino)ethyl methacrylate, and 2-(diisopropylamino)ethyl methacrylate and one or more of a positively-charged monomer selected from the group consisting of (vinylbenzyl)trimethylammonium chloride and [2-(methacryloyloxy)ethyl]trimethylammonium chloride; the ratio of pH-sensitive monomer to positively-charged monomer is about 50:50 to about 90:10, respectively; and the copolymer is in a soluble phase below a transition point and in an insoluble phase above the transition point, and wherein the transition point falls within a pH range from about 4.0 to about 9.5.

12. The method of claim 11 wherein the composition is administered with a meal.

13. The method of claim 12 wherein the meal is high in fat.

14. The method of claim 11 wherein the composition is administered orally.

15. The method of claim 11 wherein the metabolic disorder is selected from the group consisting of obesity, triglyceride levels above normal, cholestasis, and hypercholesterolemia.

* * * * *